US008124747B2

(12) United States Patent
Sablon et al.

(10) Patent No.: US 8,124,747 B2
(45) Date of Patent: Feb. 28, 2012

(54) HCV CLADE AND PROTOTYPE SEQUENCES THEREOF

(75) Inventors: Erwin Sablon, Merchtem (BE); Wim Quint, Nootdorp (NL); Leen-Jan Van Doorn, Ridderkerk (NL)

(73) Assignee: Innogenetics, Ghent (BE)

( * ) Notice: Subject to any disclaimer, the term of this patent is extended or adjusted under 35 U.S.C. 154(b) by 462 days.

(21) Appl. No.: 10/927,520

(22) Filed: Aug. 27, 2004

(65) Prior Publication Data

US 2005/0069870 A1  Mar. 31, 2005

Related U.S. Application Data

(60) Provisional application No. 60/498,654, filed on Aug. 29, 2003.

(30) Foreign Application Priority Data

Aug. 29, 2003 (EP) ..................................... 03447220

(51) Int. Cl.
C07H 23/00 (2006.01)
(52) U.S. Cl. ................... 536/23.1; 536/23.72; 536/24.3; 536/24.33; 435/5
(58) Field of Classification Search .................. None
See application file for complete search history.

(56) References Cited

U.S. PATENT DOCUMENTS

| 5,043,272 A | 8/1991 | Hartley |
| 5,077,193 A | 12/1991 | Mishiro et al. |
| 5,173,994 A | 12/1992 | Gillum et al. |
| 5,176,994 A | 1/1993 | Mishiro et al. |
| 5,252,743 A | 10/1993 | Barrett et al. |
| 5,350,671 A | 9/1994 | Houghton et al. |
| 5,372,928 A | 12/1994 | Miyamura et al. |
| 5,427,909 A | 6/1995 | Okamoto et al. |
| 5,428,145 A * | 6/1995 | Okamoto et al. ......... 536/23.72 |
| 5,514,539 A | 5/1996 | Bukh et al. |
| 5,527,669 A | 6/1996 | Resnick et al. |
| 5,550,016 A | 8/1996 | Okamoto |
| 5,620,852 A | 4/1997 | Lin et al. |
| 5,629,153 A | 5/1997 | Urdea |
| 5,629,158 A | 5/1997 | Uhlen |
| 5,820,852 A | 10/1998 | Burgess et al. |
| 5,846,704 A | 12/1998 | Maertens et al. |
| 5,871,903 A | 2/1999 | Miyamura et al. |
| 5,882,852 A | 3/1999 | Bukh et al. |
| 6,051,696 A | 4/2000 | Maertens et al. |
| 6,171,784 B1 | 1/2001 | Maertens et al. |
| 6,190,864 B1 | 2/2001 | Cha et al. |
| 6,297,370 B1 | 10/2001 | Cha et al. |
| 6,416,946 B1 | 7/2002 | Chien et al. |
| 6,495,670 B1 | 12/2002 | Maertens et al. |
| 6,548,244 B2 | 4/2003 | Maertens et al. |
| 6,762,024 B2 | 7/2004 | Maertens et al. |
| 7,067,643 B2 * | 6/2006 | Dahlberg et al. ......... 536/23.1 |
| 7,084,266 B1 * | 8/2006 | Yanagi et al. ........... 536/23.7 |
| 7,129,337 B1 * | 10/2006 | Maertens et al. ......... 536/23.1 |

FOREIGN PATENT DOCUMENTS

| EP | 0 435 229 | 7/1991 |
| EP | 0 461 863 | 12/1991 |
| EP | 0 463 848 | 1/1992 |
| EP | 0 469 348 | 2/1992 |
| EP | 0 510 952 | 10/1992 |
| EP | 0 511 559 | 11/1992 |
| EP | 0 532 167 | 3/1993 |
| EP | 0 408 918 | 11/1993 |
| EP | 0 318 216 | 12/1993 |
| EP | 0 529 493 | 12/1997 |
| EP | 0905258 A2 | 3/1999 |
| EP | 0 531 974 | 12/1999 |
| EP | 0 419 182 | 1/2000 |
| EP | 0 388 232 | 1/2005 |
| GB | 2 239 245 | 6/1991 |
| JP | 04-179482 | 6/1992 |
| JP | 06-319563 | 11/1994 |
| WO | WO 89/10977 | 11/1989 |
| WO | WO 91/06674 | 5/1991 |
| WO | WO 91/14779 | 10/1991 |
| WO | WO 92/02642 | 2/1992 |
| WO | WO 92/10588 | 6/1992 |
| WO | WO 92/19743 | 11/1992 |
| WO | WO 93/00365 | 1/1993 |
| WO | WO 93/04088 | 3/1993 |
| WO | WO 93/06126 | 4/1993 |
| WO | WO 93/10239 | 5/1993 |
| WO | WO 93/23569 | 11/1993 |
| WO | WO 94/25601 | 11/1994 |
| WO | WO 95/01442 | 1/1995 |

OTHER PUBLICATIONS

Tang et al. Hepatobiliary & Pancreatic Diseases International. 2002, vol. 1, p. 228-231.*
Howard (Journal of Gastroenterology and Hepatology, 2002, vol. 17, p. 468-470).*
Apichartpiyakul et al, Journal of Clinical Microbiology, 1994, vol. 32, No. 9, pp. 2276-2279.
Bukh et al, Proc. Natl. Acad. Sci., 1992, vol. 89, pp. 4942-4946.
Bukh et al, Proc. Natl. Acad. Sci., 1993, vol. 90, pp. 8234-8238.
Bukh et al, Proc. Natl. Acad. Sci., 1994, vol. 91, pp. 8239-8243.
Castillo et al, Journal of Virological Methods, 1992, vol. 38, pp. 71-80.
Cha et al, Journal of Clinical, Microbiology, 1991, vol. 29, pp. 2528-2534.
Cha et al, Proc. Natl. Acad. Sci., 1992, vol. 89, pp. 7144-7148.
Chan et al, Proc. Natl. Acad. Sci., 1979, vol. 76, No. 10, pp. 5036-5040.
Chan et al, Journal of General Virology, 1992, vol. 73, pp. 1131-1141.
Chayama et al, Journal of Gastroenterology and Hepatology, 1993, vol. 8, pp. 150-156.
Chen et al, Virology, 1992, vol. 188, pp. 102-113.

(Continued)

*Primary Examiner* — Agnieszka Boesen
(74) *Attorney, Agent, or Firm* — Nixon & Vanderhye P.C.

(57) ABSTRACT

The current invention relates to a previously unrecognized clade of HCV genotypes as well as to diagnostic, prophylactic and therapeutic applications of nucleic acids, proteins, and antibodies to said protein, derived of or based on the newly characterized hepatitis C viruses.

25 Claims, 4 Drawing Sheets

OTHER PUBLICATIONS

Figure 3:
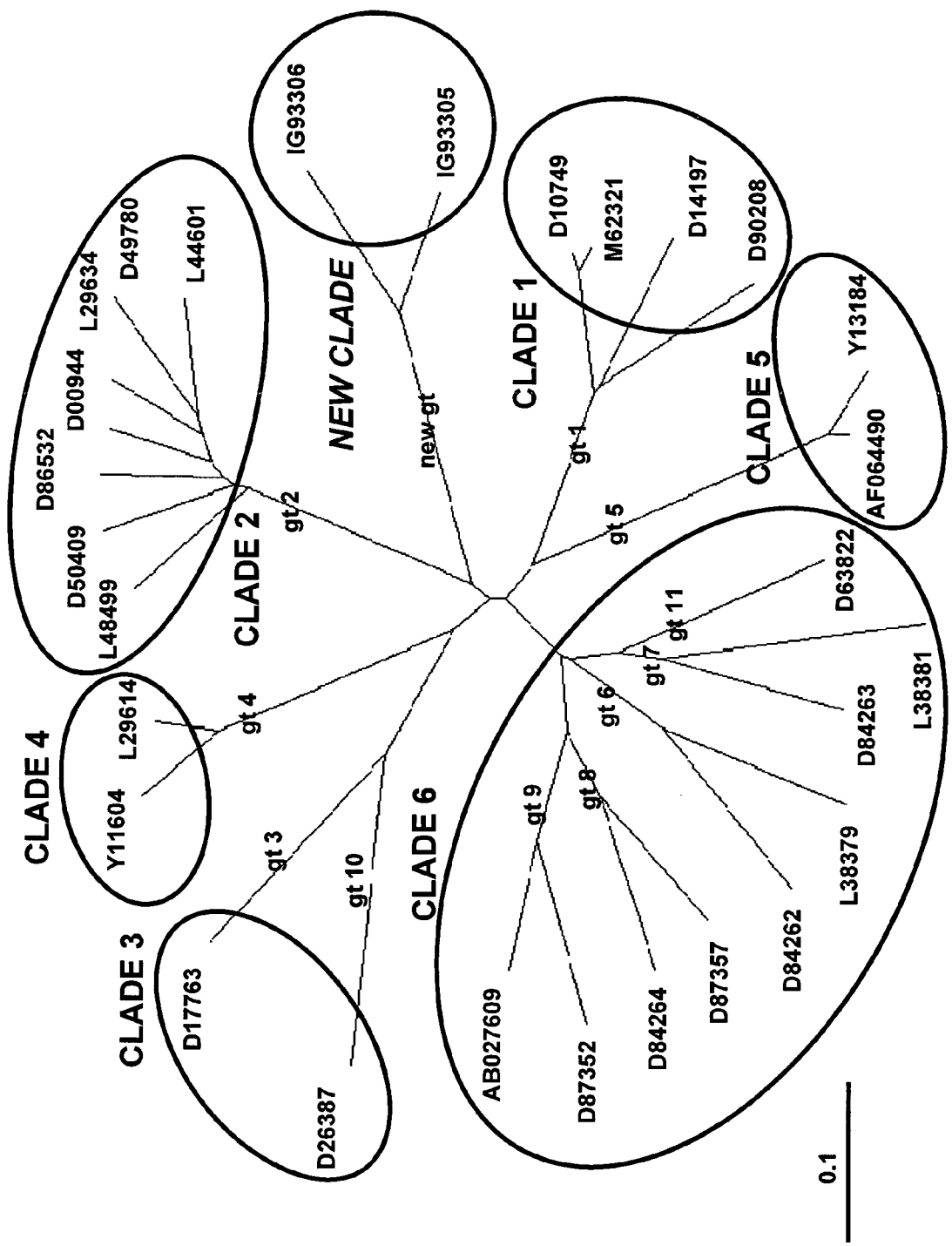

Choo et al, GenBank M62321.
Choo et al, Proc. Natl. Acad. Sci., 1991, vol. 88, pp. 2451-2455.
Co et al, Proc. Natl. Acad. Sci., 1991, vol. 88, pp. 2869-2873.
Driesel et al, Arch Virol, 1994, vol. 139, pp. 379-388.
Enomoto et al, Biochemical and Biophysical Research Communications, 1990, vol. 170, No. 3, pp. 1021-1025.
Flores et al, Nucleic Acids Research, 1990, vol. 18, No. 4, pp. 901-911.
George et al, Macromolecular Sequencing and Synthesis Selected, Methods and Applications, 1988, pp. 127-149.
Halfon et al, Journal of Clinical Microbiology, 2001, vol. 39, No. 5, pp. 1771-1773.
Han et al, Proc. Natl. Acad. Sci., 1991, vol. 88, pp. 1711-1715.
Horie et al, J. Biochem., 1989, vol. 106, pp. 1-4.
Hotta et al, GenBank D26387.
Hotta et al, Journal of Clinical Microbiology, 1994, vol. 32, No. 12, pp. 3049-3051.
Hu et al, Journal of Clinical Investigation, 1992, vol. 89, pp. 2040-2045.
Inchauspe et al, Hepatology, 1991, vol. 14, pp. 595-600.
Innis et al, In "PCR protocols. A guide to methods and applications", 1990, pp. 1-12.
Kato et al, Proc. Natl. Acad. Sci., 1990, vol. 87, pp. 9524-9528.
Kennell, Progr. Nucl. Acid Res. Mol. Biol., 1971, vol. 11, pp. 259-301.
Lee et al, Journal of Clinical Microbiology, 1992, vol. 30, No. 6, pp. 1602-1604.
Liu et al, Gene, 1992, vol. 114, pp. 245-250.
Majzoub et al, The Journal of Biological Chemistry, 1983, vol. 258, No. 23, pp. 14061-14064.
Martell et al, Journal of Virology, 1992, vol. 66, No. 5, pp. 3225-3229.
Meyerhans et al, Nucleic Acids Research, 1992, vol. 20, No. 3, pp. 521-523.
Mori et al, Biochem Biophys Res Commun, 1992, vol. 183, pp. 334-342.
Nakao et al, J Gen Virol, 1991, vol. 72, pp. 2105-2112.
Nedjar et al, Journal of Virological Methods, 1991, vol. 35, pp. 297-304.
Ogata et al, Proc. Natl. Acad. Sci., 1991, vol. 88, pp. 3392-3396.
Okamoto et al, Japan J. Exp. Med., 1990, vol. 60 No. 3, pp. 167-177.
Okamoto et al, Journal of General Virology, 1991, vol. 72, pp. 2697-2704.
Okamoto et al, Journal of General Virology, 1992, vol. 73, pp. 673-679.
Okamoto et al, Virology, 1992, vol. 188, pp. 331-341.
Qu et al, Journal of General Virology, 1994, vol. 75, pp. 1063-1070.
Rosel et al, Journal of Virology, 1985, vol. 56, No. 3, pp. 830-838.
Shuldiner et al, The Journal of Biological Chemistry, 1989, vol. 264, No. 16, pp. 9428-9432.
Simmonds et al, Journal of Clinical Microbiology, 1993, vol. 31, No. 6, pp. 1493-1503.
Simmonds et al, Journal of General Virology, 1993, vol. 74, pp. 661-668.
Sommer et al, Nucleic Acids Research, 1989, vol. 17, p. 8749.
Stratagene Catalog 1988, p. 39.
Stuyver et al, Biochemical and Biophysical Research Communications, 1993, vol. 192, No. 2, pp. 635-641.
Stuyver et al, Journal of General Virology, 1993, vol. 74, pp. 1093-1102.
Stuyver et al, Proc. Natl. Acad. Sci., 1994, vol. 91, pp. 10134-10138.
Takamizawa et al, Journal of Virology, 1991, vol. 65, No. 3, pp. 1105-1113.
van Doorn et al, GenBank L39317.
van Doorn et al, GenBank X78863.
van Doorn et al, Journal of General Virology, 1995, vol. 76, pp. 1871-1876.
van Doorn et al, Journal of Hepatology, 1994, vol. 21, pp. 122-129.
Wallace et al, Methods in Enzymology, 1987, vol. 152, pp. 432-442.
Weiner et al, Lancet, 1990, vol. 335, pp. 1-3.
Weiner et al, Virology, 1991, vol. 180, pp. 842-848.
Williams et al, Biochemistry, 1992, vol. 31, pp. 9768-9776.
Yuan et al, Proc. Natl. Acad. Sci., 1983, vol. 80, pp. 1169-1173.
Nagayama, et al., "Characteristics of hepatitis C viral genome associated with disease progression", Unpublished, Apr. 27, 2000, Database accession No. AF207756, XP002214568, Abstract.
Tokita, et al., "The entire nucleotide sequence of three hepatitis C virus isoleates in genetic groups 7-9 and comparison with those in the other eight genetic groups", Sep. 8, 1998, Database accession No. D84265, XP002214569; J. Gen. Virol., 79 (1998) 1847-1857.
Tokita, et al., "Heptatis C virus variants from Jakarta Indonesia classifiable into novel genotypes in the second (2e and 2f), tenth, (10a) and eleventh (11a) genetic groups", Database accession No. D63822, XP002214570, Abstract, J. Gen. Virol., vol. 77, 1996, pp. 293-301.
Tokita, et al., "Hepatitis C virus variants from Vietnam are classifiable into the seventh, eigth and ninth major genetic groups", Database accession No. 89955, XP002214571, Abstract, Proc. Natl. Acad. Sci. USA, vol. 91, 1994, pp. 11022-11026.
Stuyver, et al., "Hepatitis C genotyping by means of a 5'-UR/core line probe assays and molecular analysis of untypable samples", Virus Research, vol. 38, 1995, pp. 137-157, XP002057867.
Giannini, et al., "Comparative analysis of two assays for genotyping heptatitis C virus based on genotype-specific primers or probes", J. Hepatol., vol. 23, 1995, pp. 246-253, XP001104530.
Robertson, et al., "Classification, nomenclature and databse development for hepatitis C virus and related viruses: proposals for standardization", Arch. Virol., vol. 143, No. 12, 1998, pp. 24983-2503, XP001104551.
Bukh, J. "Squence analysis of the 5' noncoding region of hepatitis C virus" Proc. Natl. Acad. Sci Jun. 1992, 89:4942-4946.
Jha, J. and Arankalle, V.A., Hepatitis C. Virus Isolate NIV-10 5' Non-Coding Region, Sep. 2000, NCBI (PubMed), Nucleotide No. AF134759.
Levi et al, Journal of Clinical Microbiology, Jul. 2002, vol. 40, No. 7, pp. 2645-2647.
Tokita et al, EMBL, May 2, 1994, XP002268612.
Kurihara et al, Journal of Medical Virology, 2001, vol. 64, pp. 466-475.
Shustov et al, SWALL, Oct. 1, 2002, XP002268613.
Zibert et al, Virology, 1995, vol. 208, pp. 653-661.
Andrew Chin, On the Preparation and Utilization of Isolated and Purified Oligonucletodies, Kathrine R. Everett Law Library, University of North Carolina, CD-ROM Call No. QP625.047 C45 2002 (Feb. 14, 2003), and two pages received from Andrew Chin with letter dated May 12, 2004 and UNC Law Library Catalog record for call No. QP625.O47 C45 2002 (printed from internet on May 26, 2004).
Tokita et al, EMBL GENBAN D84265 Sep. 8, 1998 (XP-002214569).
Braasch DA, Corey DR (2001) Chem Biol. 8: 1-7. Locked nucleic acid (LNA): fine-tuning the recognition of DNA and RNA (Abstract submitted with Amendment of Dec. 31, 2007).
Mouritzen P, Nielsen AT, Pfundheller HM, Choleva Y, Kongsbak L, Møller S. (2003) Expert Rev Mol Diagn. 3: 27-38. Single nucleotide polymorphism genotyping using locked nucleic acid (LNA) (Abstract submitted with Amendment of Dec. 31, 2007).
Petersen M, Wengel J (2003) Trends Biotechnol.21: 74-81. LNA: a versatile tool for therapeutics and genomics (Abstract submitted with Amendment of Dec. 31, 2007).
Pei-Sze Ng, Bergstrom DE (2005) Nano Lett., 5: 107-111. Alternative Nucleic Acid Analogues for Programmable Assembly: Hybridization of LNA to PNA (Abstract submitted with Amendment of Dec. 31, 2007).
Simmonds et al, "Consensus Proposals for a Unified System of Nomenclature of Hepatitis C Virus Genotypes", Hepatology 2005; 42:962-973.
Beaucage et al., "Strategies in the Preparation of DNA Oligonucleotide Arrays for Diagnostic Applications", Current Medicinal Chemistry, 2001, vol. 8, No. 10, pp. 1213-1244.
Maertens et al, "Genotypes and Genetic Variation of Hepatitis C Virus", The Molecular Medicine of Viral Hepatitis, 1997, pp. 183-233.

Simmonds et al, "Classification of hepatitis C virus into six major genotypes and a series of by phylogenetic analysis of the NS-5 region", Journal of General Virology (1993), 74, 2391-2399.

US 6,180,768, 01/2001, Maertens et al. (withdrawn)

* cited by examiner

SEQ ID NO:1

CAGTCACAGAACAAGACATTCGCACTGAGACTGACATCTATCAGTGCTGTAACCTTGACCCTGA
GGCTCGCACCGTAATCACCTCCCTCACTGAGAGATTGTACGTGGGTGGCCCCATGTTCAACTCT
AGGGGCGAGAAGGTTGGCTACAGGAGGTGCAGAGCCAGTGGTGTATTCCCCACTAGCATGGGGA
ACACCATGACGTGCTATATCAAGGCCTTGGCAGCCAGCAAGGCTGCAGGCTTGGTAGGCGCGGA
TTTCCTGGTGTGTGGCGATGACTTGGTTGTCATCTGCGAGAGCAGGGGAGTCGAGCAGGACAAA
GCGGATCTGCAAGCCTTCACGGATG

SEQ ID NO:2

CAGTTACAGAACAAGACATTCGCACTGAGACTGCCATCTATCAGTGCTGCAACCTCGACCCCGA
GGCTCGCACCGCTATTGACGCCCTCACCGAGAGATTGTACGTGGGTGGTCCCATGTTCAACTCC
AAAGGTGAGAAGGTCGGATACAGAAGGTGCAGAGCCAGTGGAGTTTTCCCCACCAGCATGGGGA
ACACCATGACGTGCTACATAAAAGCCAAGGCGGCCAGCGCGGCCGCGGGCTTGAGTGGCGCCGA
TTTCCTAGTCTGTGGCGATGACCTGGTGGTCATTTGCGAGAGCAAGGGTGTCGATCAGGATAGG
GCGGCTCTGAGAGCTTTCACGGA

SEQ ID NO:3

VTEQDIRTETDIYQCCNLDPEARTVITSLTERLYVGGPMFNSRGEKVGYRRCRASGVFPTSMGN
TMTCYIKALAASKAAGLVGADFLVCGDDLVVICESRGVEQDKADLQAFTD

SEQ ID NO:4

VTEQDIRTETAIYQCCNLDPEARTAIDALTERLYVGGPMFNSKGEKVGYRRCRASGVFPTSMGN
TMTCYIKAKAASAAAGLSGADFLVCGDDLVVICESKGVDQDRAALRAFT

FIGURE 1

SEQ ID NO:16

GGTCAACAGTCAGCGAACGYTCCGAGCGTGTTTGCTGTTCAATGTCCTACTCATGGACGGGAGC
CTTAGTGACGCCCTCCGGACCGGAGGAGGAAAGGCTTCCGATAAATGCCCTGAGCAACACCATG
CTACGGCATTACAACATGGTTTACAGCACAACATCACGCTCGGCCGCTCAGAGGGCAAAGAAAG
TGACTTTTGACAGACTGCAAGTTCTCGATGACCACTACAAGAGAACGCTCGATGACGTCAAGGC
TAAGGCCGCTGGCGTTACCGCACGTTTGCTCACCTTGGAGGAGGCTGCCGCTCTTACTCCGACC
CACTCCGCGAGATCTAAGTTCGGGTATGGGGCGAAGGATGTGAGAGCTCTCGCCCCCAAGGCAG
TGACTGACATAAAAGGAGTCTGGAAGAACTTGCTTACTGACAAGACTACCCCGATACCGACTTC
AATAATGGCCAAGAATGAGGTCTTCTGTGTTAACCCTGCYAAGGGAGGGAAAAAACCAGCTAGA
CTGATTGTATACCCTGACTTAGGCGTCCGGGTGTGCGAGAAGCGAGCGCTGTACGATCTAGCGC
AAAAGCTTCCTCAGGCCGTTATGGGGTCCGCATACGGGTTCCAATACTCACCTGCTCAGCGGGT
TGATCTCCTGGTTAAGACGTGGGAGTCCAAACGCACTCCCATGGGCTTTTCATATGATACCCGC
TGTTTTGACTCTACAGTTACAGAACAAGACATTCGCACTGAGACTGCCATCTATCAGTGCTGCA
ACCTCGACCCCGAGGCTCGCACCGCTATTGACGCCCTCACCGAGAGATTGTACGTGGGTGGTCC
CATGTTCAACTCCAAAGGTGAGAAGGTCGGATACAGAAGGTGCAGAGCCAGTGGAGTTTTCCCC
ACCAGCATGGGGAACACCATGACGTGCTACATAAAAGCCAAGGCGGCCAGCGCGGCCGCGGGCT
TGAGTGGCGCCGATTTCCTAGTCTGTGGCGATGACCTGGTGGTCATTTGCGAGAGCAAGGGTGT
CGATCAGGATAGGGCGGCTCTGAGAGCTTTCACGGA

SEQ ID NO:17

STVSERSERVCCSMSYSWTGALVTPSGPEEERLPINALSNTMLRHYNMVYSTTSRSAAQRAKKV
TFDRLQVLDDHYKRTLDDVKAKAAGVTARLLTLEEAAALTPTHSARSKFGYGAKDVRALAPKAV
TDIKGVWKNLLTDKTTPIPTSIMAKNEVFCVNPAKGGKKPARLIVYPDLGVRVCEKRALYDLAQ
KLPQAVMGSAYGFQYSPAQRVDLLVKTWESKRTPMGFSYDTRCFDSTVTEQDIRTETAIYQCCN
LDPEARTAIDALTERLYVGGPMFNSKGEKVGYRRCRASGVFPTSMGNTMTCYIKAKAASAAAGL
SGADFLVCGDDLVVICESKGVDQDRAALRAFT

FIGURE 2

SEQ ID NO:9

```
     -260        -250        -240        -230        -220
      |     |     |     |     |     |     |     |     |     |
TTTCTAGCCATGGCGTTAGTATGAGTGTCGTACAGCCTCCAGGACCCCCC
     -210        -200        -190        -180        -170
      |     |     |     |     |     |     |     |     |
CTCCCGGGAGAGCCATAGTGGTCTGCGGAACCGGTGAGTACACCGGAATT
     -160        -150        -140        -130        -120
      |     |     |     |     |     |     |     |     |
GCCGGGAAGACTGGGTCCTTTCTTGGATTAACCCACTCTATGCCCGGAGA
     -110        -100         -90         -80         -70
      |     |     |     |     |     |     |     |     |
TTTGGGCGTGCCCCCGCGAGACTGCTAGCCGAGTAGTGTTGGGTCGCGAA
      -60         -50         -40         -30
      |     |     |     |     |     |     |     |
AGGCCTTGTGGTACTGCCTGATAGGGTGCTTGCGAGTGA
```

SEQ ID NO:10

```
     -260        -250        -240        -230        -220
      |     |     |     |     |     |     |     |     |     |
TTTCTAGCCATGGCGTTAGTATGAGTGTCGTACAGCCTCCAGGACCCCCC
     -210        -200        -190        -180        -170
      |     |     |     |     |     |     |     |     |
CTCCCGGGAGAGCCATAGTGGTCTGCGGAACCGGTGAGTACACCGGAATT
     -160        -150        -140        -130        -120
      |     |     |     |     |     |     |     |     |
GCCGGGAAGACTGGGTCCTTTCTTGGATAAACCCACTCTATGCCCGGAGA
     -110        -100         -90         -80         -70
      |     |     |     |     |     |     |     |     |
TTTGGGCGTGCCCCCGCGAGACTGCTAGCCGAGTAGTGTTGGGTCGCGAA
      -60         -50         -40         -30
      |     |     |     |     |     |     |     |
AGGCCTTGTGGTACTGCCTGATAGGGTGCTTGCGAGTGA
```

FIGURE 4

US 8,124,747 B2

HCV CLADE AND PROTOTYPE SEQUENCES THEREOF

The present application claims benefit of U.S. Provisional Application No. 60/498,654, filed 29 Aug. 2003 and EP 03447220.9 filed 29 Aug. 2003, the entire contents of each of which is hereby incorporated herein by reference.

FIELD OF THE INVENTION

The current invention relates to a previously unrecognized clade of HCV genotypes as well as to diagnostic, prophylactic and therapeutic applications of nucleic acids, proteins, and antibodies to said protein, derived of or based on the newly characterized hepatitis C viruses.

BACKGROUND OF THE INVENTION

The about 9.6 kb single-stranded RNA genome of the HCV virus comprises a 5'- and 3'-non-coding region (NCRs) and, in between these NCRs a single long open reading frame of about 9 kb encoding an HCV polyprotein of about 3000 amino acids.

HCV polypeptides are produced by translation from the open reading frame and cotranslational proteolytic processing. Structural proteins are derived from the amino-terminal one-fourth of the coding region and include the capsid or Core protein (about 21 kDa), the E1 envelope glycoprotein (about 35 kDa) and the E2 envelope glycoprotein (about 70 kDa, previously called NS1), and p7 (about 7 kDa). The E2 protein can occur with or without a C-terminal fusion of the p7 protein (Shimotohno et al. 1995). Recently, an alternative open reading frame in the Core-region was found which is encoding and expressing a protein of about 17 kDa called F (Frameshift) protein (Xu et al. 2001; Ou & Xu in U.S. patent application Publication No. US2002/0076415). In the same region, ORFs for other 14-17 kDa ARFPs (Alternative Reading Frame Proteins), A1 to A4, were discovered and antibodies to at least A1, A2 and A3 were detected in sera of chronically infected patients (Walewski et al. 2001). From the remainder of the HCV coding region, the non-structural HCV proteins are derived which include NS2 (about 23 kDa), NS3 (about 70 kDa), NS4A (about 8 kDa), NS4B (about 27 kDa), NS5A (about 58 kDa) and NS5B (about 68 kDa) (Grakoui et al. 1993).

The sequences of cDNA clones covering the complete genome of several prototype isolates have been determined and include complete prototype genomes of the HCV genotypes 1a (e.g., GenBank accession number AF009606), 1b (e.g., GenBank accession number AB016785), 1c (e.g., GenBank accession number D14853), 2a (e.g., GenBank accession number AB047639), 2b (e.g., GenBank accession number AB030907), 2c (e.g., GenBank accession number D50409) 2k (e.g., GenBank accession number AB031663), 3a (e.g., GenBank accession number AF046866), 3b (e.g., GenBank accession number D49374), 4a (e.g., GenBank accession number Y11604), 5a (e.g., GenBank accession number AF064490), 6a (e.g., GenBank accession number Y12083), 6b (e.g., GenBank accession number D84262), 7b (e.g., GenBank accession number D84263), 8b (e.g., GenBank accession number D84264), 9a (e.g., GenBank accession number D84265), 10a (e.g., GenBank accession number D63821) and 11a (e.g., GenBank accession number D63822).

At present 11 genotypes of HCV are known which can be classified into 6 clades (or major lineages). Thus, HCV genotypes 1, 2, 4, and 5 are identified as clades 1, 2, 4 and 5, respectively; HCV genotypes 3 and 10 belong to clade 3; and HCV genotypes 6, 7, 8, 9 and 11 are members of lade 6 (Robertson et al. 1998). The current classification system is based on a threefold hierarchy. Basically, the classification system distinguishes, based on percentage of mutual homologies between sequences, between:

- HCV isolates belonging to different types;
- HCV isolates belonging to the same type but to a different subtype; and
- HCV isolates belonging to the same subtype (Maertens and Stuyver 1997).

Nucleic acid and amino acid sequences of HCV genotypes 1 to 11 have been disclosed not only in public databases but also in, e.g., International Patent Publications WO94/12670, WO94/25601, and WO96/13590. A further new HCV genotype different from genotypes 6-9 and 11 but belonging to clade 6 has recently been disclosed in International Patent Publication WO 03/020970. Further new subtypes of HCV genotype 2 (clade 2) and a new subtype of HCV genotype 1 (clade 1) have been described by Candotti et al. (2003).

SUMMARY OF THE INVENTION

The present invention relates in a first aspect to an isolated nucleic acid comprising an HCV nucleic acid sequence of an HCV clade represented by any of the following HCV nucleic acid sequences which are prototype sequences of said HCV clade:

(i) a nucleic acid sequence defined by SEQ ID NOs: 1, 2, 9, 10 or 16;
(ii) a nucleic acid sequence encoding a protein defined by SEQ ID NOs: 3, 4 or 17;
(iii) a nucleic acid sequence which is the complement of a nucleic acid sequence of (i) or (ii);
(iv) a nucleic acid sequence hybridizing to a nucleic acid sequence of (i), (ii) or (iii) under stringent conditions;
wherein said nucleic acid is DNA, cDNA or a synthetic nucleic acid, or
wherein said nucleic acid is RNA and wherein "T" is replaced by "U".

Alternatively the invention covers an isolated nucleic acid comprising an HCV nucleic acid sequence of an HCV genotype represented by any of the following HCV nucleic acid sequences which are prototype sequences of said HCV genotype:

(i) a nucleic acid sequence defined by SEQ ID NOs: 1, 2, 9, 10 or 16 wherein SEQ ID NOs: 1 and 9 and SEQ ID NOs: 2, 10 and 16 each represent a different subtype of said HCV genotype;
(ii) a nucleic acid sequence encoding a protein defined by SEQ ID NOs: 3, 4 or 17;
(iii) a nucleic acid sequence which is the complement of a nucleic acid sequence of (i) or (ii);
(iv) a nucleic acid sequence hybridizing to a nucleic acid sequence of (i), (ii) or (iii) under stringent conditions;
wherein said nucleic acid is DNA, cDNA or a synthetic nucleic acid, or
wherein said nucleic acid is RNA and wherein "T" is replaced by "U".

In a further aspect, the invention envisages oligonucleotides comprising at least 8 contiguous nucleotides taken from an HCV nucleic acid sequence according to the invention and wherein said oligonucleotide comprises at least one nucleotide that is different from any HCV nucleic acid sequence of an HCV of clades 1 to 6 or different from any HCV nucleic acid sequence of an HCV genotype or subtype of clades 1 to 6.

Said oligonucleotide can be a primer capable of directing specific amplification of an HCV nucleic acid sequence according to the invention. Alternatively, said oligonucleotide can be a probe capable of specifically hybridizing to an HCV nucleic acid sequence according to the invention. In a further alternative, said oligonucleotide is capable of specifically detecting an HCV nucleic acid sequence according to the invention.

Any of the nucleic acid sequences or oligonucleotides of the invention can comprise besides ribonucleic acid monomers or deoxyribonucleic acid monomers: one or more modified nucleotide bases, one or more labeled nucleotides, one or more peptide nucleic acid monomers, one or more locked nucleic acid monomers, and/or the backbone of said nucleic acid or oligonucleotide can be modified.

Another aspect of the invention relates to isolated proteins comprising an HCV amino acid sequence encoded by an HCV nucleic acid sequence according to the invention. In a specific embodiment thereto, said isolated protein is defined by an amino acid sequence is defined by SEQ ID NOs:3, 4 or 17. Further included in the present invention are peptides of at least 5 contiguous amino acids taken from an HCV amino acid sequence according to the invention and wherein said peptide comprises at least one amino acid that is different from any HCV amino acid sequence of an HCV of clades 1 to 6 or different from any HCV amino acid sequence of an HCV genotype or subtype of clades 1 to 6. If the HCV amino acid sequence in a protein or peptide of the invention is comprising at least one cysteine, said cysteine can be reversibly or irreversibly protected.

In another aspect, the current invention envisages recombinant vectors comprising a nucleic acid or oligonucleotide according to the invention. More specifically, said recombinant vector can be an expression vector capable of directing expression of an HCV protein encoded by the HCV nucleic acid sequence comprised in said vector.

Host cells transformed with a nucleic acid or oligonucleotide according to the invention or transformed with a recombinant vector according to the invention are also part of the present invention.

The invention further covers methods for detecting the presence of an HCV virus in a biological sample and/or for determining the genotype of said HCV virus comprising the step of detecting the presence of a nucleic acid or oligonucleotide according to the invention. In any of these methods the detection of the presence of said HCV nucleic acid sequence can be based on at least one of an amplification reaction, a sequencing reaction, a hybridization reaction or a reverse hybridization reaction wherein in any of said reaction an oligonucleotide according to the prevention can be used.

The invention further relates to diagnostic kits for detecting the presence and/or for determining the genotype of an HCV virus in a biological sample, said kit comprising at least one of a nucleic acid or an oligonucleotide according to the invention. In said kit, said nucleic acids or oligonucleotides can be attached to a solid support.

The invention also relates to methods for detecting antibodies to an HCV virus present in a biological sample and/or a method of typing said HCV virus comprising the step of detecting said antibodies with at least one protein or peptide according to the invention.

Diagnostic kits for detecting antibodies to an HCV virus or for typing of an HCV virus wherein said kits comprise at least one protein or peptide according to the invention are part of the invention. In said diagnostic kit said protein or peptide can be bound to a solid support.

Another aspect of the invention relates to antibodies raised upon immunization of a mammal with at least one protein or peptide according to the invention. Said antibodies can be monoclonal antibodies or humanized antibodies. Said antibodies can be employed in methods for detecting the presence of HCV antigens in a biological sample and/or for typing of an HCV virus present in a biological sample.

The invention further relates to methods for detecting antibodies to an HCV virus present in a biological sample comprising contacting an antigen with said antibodies in the presence of an isolated antibody according to the invention as competitor of binding of said antigen to said antibody.

Another method of the invention is detecting the presence of HCV antigens in a biological sample comprising contacting said antigen with an antibody to said antigen in the presence of an isolated protein or peptide according to the invention as competitor of binding of said antigen to said antibody.

Further diagnostic kits part of the invention are kits for detecting the presence of HCV antigens, said kit comprising at least an antibody according to the invention. Diagnostic kits for detecting the presence of HCV antigens, said kits comprising at least one isolated protein or peptide according to the invention are also envisaged.

Another aspect of the invention relates to compositions, immunogenic compositions and/or vaccine compositions comprising at least one of an nucleic acid or oligonucleotide according to the invention, an isolated protein or peptide according to the invention, a recombinant vector according to the invention or an antibody according to the invention; and at least one of a suitable carrier, adjuvant or vehicle. In particular said immunogenic compositions are HCV immunogenic compositions and said vaccine compositions are HCV vaccine compositions, therapeutic HCV vaccine compositions or prophylactic HCV vaccine compositions. Any of these compositions can be used for immunizing a mammal against HCV infection or for treating a mammal infected with HCV.

A further aspect of the invention relates to a method for the recombinant production of a protein or peptide according to the invention comprising the steps of:
(i) transformation of an appropriate cellular host with a recombinant vector according to the invention;
(ii) culturing the transformed cellular host of (i) under conditions enabling the expression of said protein;
(iii) harvesting the protein expressed in (ii).

The invention further relates to an isolated HCV virus characterized by a genome comprising an HCV nucleic acid sequence of a nucleic acid or oligonucleotide according to the invention.

The invention further relates to a method for determining the genotype of an HCV nucleic acid or oligonucleotide according to the invention comprising the identification of the regions −100 to −92 and −128 to −118 in the 5' non-coding region of the genome of said virus. Said method can further comprise identification of at least one of the regions −138 to −132 or −240 to −233 in the 5' non-coding region of the genome of said virus. In particular, said region −100 to −92 is defined by SEQ ID NO: 11 or the complement thereof or any thereof wherein "T" is replaced by "U". In particular, said region −128 to −118 is defined by SEQ ID NO: 12 or the complement thereof or any thereof wherein "T" is replaced by "U". In particular, said region −138 to −132 is defined by SEQ ID NOs:13 or 14 or the complement thereof or any thereof wherein "T" is replaced by "U". In particular, said region −240 to −223 is defined by SEQ ID NO: 15 or the complement thereof or any thereof wherein "T" is replaced by "U".

FIGURE LEGENDS

FIG. 1. Nucleotide and amino acid sequences of NS5B region of HCV isolates IG93305 and IG93306. SEQ ID NO:1

(nucleotide sequence of part of the NS5B region of HCV isolate IG93305, 345 nt), SEQ ID NO:2 (nucleotide sequence of part of the NS5B region of HCV isolate IG93306, 343 nt), SEQ ID NO:3 (amino acid sequence of part of the NS5B region of HCV isolate IG93305, 114 aa), SEQ ID NO:4 (amino acid sequence of part of the NS5B region of HCV isolate IG93306, 113 aa).

FIG. 2. Extended nucleotide and amino acid sequences of NS5B region of HCV isolate IG93306. SEQ ID NO:16 (nucleotide sequence of part of the NS5B region of HCV isolate IG93306, 1060 nt), SEQ ID NO: 17 (amino acid sequence of part of the NS5B region of HCV isolate IG93306, 352 aa). Within SEQ ID NOs: 16 and 17 are underlined SEQ ID NOs: 2 and 4, respectively (see FIG. 1).

FIG. 3. Phylogenetic tree resulting from phylogenetic analysis with bootstrap analysis (n=1000) of the NS5B nucleotide sequences (SEQ ID NO:1 and 2) relative to the NS5B nucleotide sequences of the indicated isolates of the indicated genotypes (gt1 to gt11 wherein "gt" stands for genotype). The 6 known HCV clades are circled and indicated as "Clade 1" to "Clade 6". The new HCV clade identified in the present invention and harboring as prototype NS5B sequences SEQ ID NO: 1 and 2 is indicated as "New clade" and the new genotype representing the new clade is indicated as "new gt". The scale bar represents the scaled evolutionary distance.

FIG. 4. Nucleotide sequences of the 5' non-coding region or untranslated region (5'NCR or 5'UTR) of HCV isolates IG93305 (SEQ ID NO:9) and IG93306 (SEQ ID NO:10). Indicated are the nucleotide numbers relative to the adenine in the start codon of the HCV polyprotein whereby the first nucleotide 5' upstream of said adenine is numbered "−1". Nucleotide differences between the two sequences are double underlined.

DETAILED DESCRIPTION OF THE INVENTION

All of the HCV variants characterized since the initial molecular characterization of HCV in 1989 occurred are classified in 6 HCV clades comprising at least 12 major genotypes and more than 70 subtypes. The most recently identified new HCV variants (WO 03/020970; Candotti et al. (2003)) fit within the existing HCV clades/genotypes. The finding, as outlined in the present invention, of new HCV variants fitting which do not fit into one of the existing HCV clades but instead form a new HCV clade is therefore highly unexpected. This finding will also further add to the sensitivity and specificity of HCV diagnosis (and thus primary prevention of HCV spread) and will further add to the development of prophylactic and therapeutic HCV compositions.

New HCV genotype characterized today is initially identified as one or a few HCV nucleic acid sequences that are prototype sequences for said HCV genotype. These prototype HCV sequences are identified by phylogenetic analysis of at least the nucleic acid sequence of the NS5B region of the HCV genome: whereas Robertson et al. (1998) advise to run the phylogenetic analysis on the Core, E1 or NS5B sequences, Salemi and Vandamme (2002) reported that the NS5B region has the highest phylogenetic signal and can be employed reliably for phylogenetic analysis when the full-genome sequence is not (yet) available. The phylogenetic analysis method generally accepted by the HCV research community is based on the neighbor joining method applying the Kimura 2-parameter model (e.g. Robertson et al. 1998). As a reference in the phylogenetic analysis are taken previously genotyped HCV sequences representing all known genotypes. The neighbour-joining method is explained in Saitou and Nei (1987), the Kimura parameters are described by Kimura (1980) and the advantage of combining the two is disclosed by, e.g., Tateno et al. (1994).

The terms nucleic acid and polynucleic acid are used interchangeably herein.

The present invention relates in a first aspect to an isolated nucleic acid comprising an HCV nucleic acid sequence of an HCV clade represented by any of the following HCV nucleic acid sequences which are prototype sequences of said HCV lade:

(i) a nucleic acid sequence defined by SEQ ID NOs: 1, 2, 9, 10 or 16;

(ii) a nucleic acid sequence encoding a protein defined by SEQ ID NOs: 3, 4 or 17;

(iii) a nucleic acid sequence which is the complement of a nucleic acid sequence of (i) or (ii);

(iv) a nucleic acid sequence hybridizing to a nucleic acid sequence of (i), (ii) or (iii) under stringent conditions;

wherein said nucleic acid is DNA, cDNA or a synthetic nucleic acid, or wherein said nucleic acid is RNA and wherein "T" is replaced by "U".

Alternatively the invention covers an isolated nucleic acid comprising an HCV nucleic acid sequence of an HCV genotype represented by any of the following HCV nucleic acid sequences which are prototype sequences of said HCV genotype:

(i) a nucleic acid sequence defined by SEQ ID NOs: 1, 2, 9, 10 or 16 wherein SEQ ID NOs: 1 and 9 and SEQ ID NOs:2, 10 and 16 each represent a different subtype of said HCV genotype;

(ii) a nucleic acid sequence encoding a protein defined by SEQ ID NOs: 3, 4 or 17;

(iii) a nucleic acid sequence which is the complement of a nucleic acid sequence of (i) or (ii);

(iv) a nucleic acid sequence hybridizing to a nucleic acid sequence of (i), (ii) or (iii) under stringent conditions;

wherein said nucleic acid is DNA, cDNA or a synthetic nucleic acid, or wherein said nucleic acid is RNA and wherein "T" is replaced by "U".

Herein SEQ ID NOs:1, 2 and 16 are NS5B nucleic acid sequences of two individual HCV isolates fitting in the new clade identified in the current invention. SEQ ID NOs: 9 and 10 are 5'non-coding region nucleic acid sequences of said HCV isolates. SEQ ID NOs:3, 4 and 17 are the NS5B amino acid sequences derived from SEQ ID NOs: 1, 2 and 16, respectively.

In a further aspect, the invention envisages oligonucleotides comprising at least 8 contiguous nucleotides taken from an HCV nucleic acid sequence according to the invention and wherein said oligonucleotide comprises at least one nucleotide that is different from any HCV nucleic acid sequence of an HCV of clades 1 to 6 or different from any HCV nucleic acid sequence of an HCV genotype or subtype of clades 1 to 6.

Said oligonucleotide can be a primer capable of directing specific amplification of an HCV nucleic acid sequence according to the invention. Alternatively, said oligonucleotide can be a probe capable of specifically hybridizing to an HCV nucleic acid sequence according to the invention. In a further alternative, said oligonucleotide is capable of specifically detecting an HCV nucleic acid sequence according to the invention.

Any of the nucleic acid sequences or oligonucleotides of the invention can comprise besides ribonucleic acid monomers or deoxyribonucleic acid monomers: one or more modified nucleotide bases, one or more labeled nucleotides, one or more peptide nucleic acid monomers, one or more locked nucleic acid monomers, and/or the backbone of said nucleic acid or oligonucleotide can be modified.

With "at least 1 nucleotide different from any HCV nucleic acid of an HCV of clades 1 to 6" is meant an HCV nucleic acid according to the invention that has anywhere in its nucleic acid sequence at least 1 nucleotide that is different from the corresponding nucleotide in an HCV nucleic acid sequence of any genotype, subtype or isolate of an HCV classifying in any of the known clades 1 to 6. "Corresponding nucleotide" in this context is referring to a nucleotide at the same relative position in the HCV genome (whether noted as RNA or DNA) wherein the relative position takes into account the possibly occurring genotype-, subtype-, or isolate-specific insertions and/or deletions (see for instance section on Genotype-specific insertions and deletions on page 198 of Maertens and Stuyver, 1997); a corresponding nucleotide can also be present in a nucleic acid that is the complement of the nucleic acid to which the comparison is made. Differences between nucleotide sequences can easily be determined by the skilled person, for instance after aligning said sequences. Equivalents of or alternatives for "at least 1 nucleotide different from any HCV nucleic acid of an HCV of clades 1 to 6" include "at least 1 nucleotide that is specific to an HCV nucleic acid sequence of the present invention" or "at least 1 nucleotide that is unique to an HCV nucleic acid sequence of the present invention". A further equivalent or alternative includes "at least 1 genotype-specific nucleotide" wherein genotype-specific is referring to the specificity or uniqueness of a nucleotide to an HCV nucleotide sequence of an HCV genotype of the newly identified HCV clade of the present invention that is different from any of the HCV clades 1 to 6. The term "genotype-specific" is generally accepted as can for instance be derived from EP 0 637 342 B1 or any of U.S. Pat. No. 6,548,244, U.S. Pat. No. 5,882,852 or U.S. Pat. No. 5,514,539. The terms "different from", "unique to", "specific to", "corresponding" described above in relation to nucleotides are equally valid in relation to amino acids. The skilled person will understand that this implies exchanging in the above explanation "nucleotide" for "amino acid", "nucleic acid sequence" for "amino acid sequence", "nucleic acid" for "protein", etc. The unique or specific nucleotides/amino acids as outlined above can occur as a single nucleotide/amino acid or a set of nucleotides/amino acids specific to a nucleic acid/amino acid sequence of any of the new HCV types identified in the present invention. The specific or unique nucleotides/amino acids of said set can form a contiguous sequence or can be dispersed in a larger region of a nucleic acid/amino acid sequence of any of the new HCV types identified in the present invention.

A "nucleotide" is meant to include any naturally occurring nucleotide as well as any modified nucleotide wherein said modification can occur in the nucleotide base or the nucleotide sugar. Any of the modifications can be introduced in a nucleic acid or oligonucleotide to increase/decrease stability and/or reactivity of the nucleic acid or oligonucleotide and/or for other purposes such as labeling of the nucleic acid or oligonucleotide. Modified nucleotides include phophorothioates, alkylphophorothioates, methylphosphonate, phosphoramidate, peptide nucleic acid monomers and locked nucleic acid monomers.

A polynucleic acid, nucleic acid and oligonucleotide may be of genomic origin, may be DNA, RNA, cDNA, may be the product of chemical synthesis, may comprise modified nucleotides, or may be hybrids of DNA and/or RNA and/or modified nucleotides. A polynucleic acid, nucleic acid can be single- or double-stranded or may be a triplex-forming nucleic acid.

"Nucleotide acid amplification" is meant to include all methods resulting in multiplication of the number of a target nucleic acid. Nucleotide sequence amplification methods include the polymerase chain reaction (PCR; DNA amplification), strand displacement amplification (SDA; DNA amplification), transcription-based amplification system (TAS; RNA amplification), self-sustained sequence replication (3SR; RNA amplification), nucleic acid sequence-based amplification (NASBA; RNA amplification), transcription-mediated amplification (TMA; RNA amplification), Qbeta-replicase-mediated amplification and run-off transcription. During amplification, the amplified products can be conveniently labeled either using labeled primers or by incorporating labeled nucleotides. Labels may be isotopic ($^{32}P$, $^{35}S$, etc.) or non-isotopic (biotin, digoxigenin, etc.).

The most widely spread nucleotide sequence amplification technique is PCR. Basically, two primers, a sense and an antisense are annealed to a denatured DNA substrate and extended by a thermostable DNA polymerase. The latter allows rapid and repeated thermal cycling (denaturing/annealing/extension in three-step PCR; denaturing/annealing+extension in two-step PCR). The target DNA is exponentially amplified. The amplification reaction is repeated between 20 and 70 times, advantageously between 25 and 45 times. Many methods rely on PCR including AFLP (amplified fragment length polymorphism), IRS-PCR (interspersed repetitive sequence PCR), iPCR (inverse PCR), RAPD (rapid amplification of polymorphic DNA), RT-PCR (reverse transcription PCR) and real-time PCR. RT-PCR can be performed with a single thermostable enzyme having both reverse transcriptase and DNA polymerase activity (Myers et al., 1991). Alternatively, a single tube-reaction with two enzymes (reverse transcriptase and thermostable DNA polymerase) is possible (Cusi et al., 1994).

The term "oligonucleotide" is meant to include all nucleic acid molecules comprising or consisting of a part of the HCV nucleic acids according to the invention. The lower size limit of an oligonucleotide is a nucleic acid comprising or consisting of at least 5 contiguous nucleotides of the HCV nucleic acids according to the invention. An oligonucleotide thus can comprise or consist of at least and/or comprise or consist of up to 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 or more contiguous nucleotides of an HCV nucleic acid according to the invention.

A "primer capable of directing specific amplification of a nucleic acid" is the at least one oligonucleotide in a nucleic acid amplification reaction mixture that is required to obtain specific amplification of a target nucleic acid. Nucleic acid amplification can be linear or exponential and can result in an amplified single nucleic acid of a single- or double-stranded nucleic acid or can result in both strands of a double-stranded nucleic acid. Specificity of a primer in directing amplification of a nucleic acid can be improved by introducing modified nucleotides in said primer. The fact that a primer does not have to match exactly with the corresponding template or target sequence to warrant specific amplification of said template or target sequence is amply documented in literature (for instance: Kwok et al. 1990). Primers as short as 8 nucleotides in length have been applied successfully in directing specific amplification of a target nucleic acid molecule (for instance: Majzoub et al. 1983).

A "probe capable of specifically hybridizing with a nucleic acid" is an oligonucleotide mainly hybridizing to one specific nucleic acid sequence in a mixture of many different nucleic acid sequences. Specific hybridization is meant to result, upon detection of the specifically formed hybrids, in a signal-to-noise ratio (wherein the signal represents specific hybridization and the noise represents unspecific hybridization) sufficiently high to enable unambiguous detection of said specific hybrids. In a specific case specific hybridization allows discrimination of up to a single nucleotide mismatch between the probe and the target nucleic acids. Conditions allowing specific hybridization generally are stringent but can obviously be varied depending on the complexity (size, GC-content, overall identity, etc.) of the probe(s) and/or target nucleic acid molecules. Specificity of a probe in hybridizing with a nucleic acid can be improved by introducing modified nucleotides in said probe.

An oligonucleotide according to the present invention may further comprise a modification for attaching said oligonucleotide to a solid support. Said modification may for instance be an amine-, thiol-, 3-'propanolamine or Acrydite-modification of the oligonucleotide or may comprise the addition of a homopolymeric tail (for instance an oligo(dT)-tail added enzymatically via a terminal transferase enzyme or added synthetically) to the oligonucleotide. If said homopolymeric tail is positioned at the 3'-terminus of the oligonucleotide or if any other 3'-terminal modification preventing enzymatic extension is incorporated in the oligonucleotide, the priming capacity of the oligonucleotide can be decreased or abolished. Other modifications are described in for instance Beaucage et al. (2001).

The present invention relates to probes comprising part of an HCV polynucleic acid as defined herein, with said probe being able to act as a hybridization probe for specific detection and/or classification into types and/or subtypes of HCV nucleic acids present in and/or obtained from a biological sample, with said probe being optionally labeled or attached to a solid substrate.

A "HCV polynucleic acid" or, in particular, an "isolated HCV polynucleic acid" is meant to comprise single-stranded polynucleic acids, double-stranded polynucleic acids or triplex-forming polynucleic acids obtained directly from a sample or obtained after duplication, multiplication or amplification; or obtained after chemical synthesis. "Obtained" is, in the present context, meant to include isolation and/or purification and/or amplification of said polynucleic acids from a biological sample. The "sample" may be any biological material taken either directly from an infected human being (or animal), or after culturing (enrichment). Biological material may be e.g. expectorations of any kind, broncheolavages, blood, serum, plasma, skin tissue, biopsies, sperm, lymphocyte blood culture material, colonies, liquid cultures, faecal samples, urine etc. Biological material may also be artificially infected cell cultures or the liquid phase thereof. The term "biological sample" generally refers to any biological sample (tissue or fluid) containing HCV nucleic acid sequences and refers more particularly to blood serum or plasma samples. "Duplication, multiplication or amplification" is meant to include any nucleic acid amplification method producing a nucleic acid. Said amplification methods also include sequencing. Thus, any sequencing technique producing a nucleic acid molecule comprising part or all of the HCV nucleic acids according to the present invention is to be understood to be comprised in the term "duplication, multiplication or amplification".

Solid phases, solid matrices or solid supports on which molecules, e.g., the nucleic acids, oligonucleotides or proteins or peptides of the present invention, may be bound (or captured, absorbed, adsorbed, linked, coated, immobilized; covalently or non-covalently) comprise beads or the wells or cups of microtiter plates, or may be in other forms, such as solid or hollow rods or pipettes, particles, e.g., from 0.1 μm to 5 mm in diameter (e.g. "latex" particles, protein particles, or any other synthetic or natural particulate material), microspheres or beads (e.g. protein A beads, magnetic beads). A solid phase may be of a plastic or polymeric material such as nitrocellulose, polyvinyl chloride, polystyrene, polyamide, polyvinylidine fluoride or other synthetic polymers. Other solid phases include membranes, sheets, strips, films and coatings of any porous, fibrous or bibulous material such as nylon, polyvinyl chloride or another synthetic polymer, a natural polymer (or a derivative thereof) such as cellulose (or a derivative thereof such as cellulose acetate or nitrocellulose). Fibers or slides of glass, fused silica or quartz are other examples of solid supports. Paper, e.g., diazotized paper may also be applied as solid phase. Clearly, molecules, in casu the nucleic acids, oligonucleotides, proteins or peptides of the present invention, may be bound, captured, absorbed, adsorbed, linked or coated to any solid phase suitable for use in hybridization assay (irrespective of the format, for instance capture assay, reverse hybridization assay, DASH or dynamic allele-specific hybridization wherein the "alleles" are the nucleic acids of different HCV genotypes, -subtypes, or -isolates) or in an immunoassays. Said molecules, in casu the nucleic acids, oligonucleotides, proteins or peptides of the present invention, can be present on a solid phase in defined zones such as spots or lines.

Any of the solid phases described above can be developed, e.g. automatically developed in an assay device.

With "developed" or "development" is meant that a sample or samples, suspected of comprising a binding partner to a molecule present on a solid phase, is or are applied to said solid phase and that the necessary steps are performed in order to detect binding of the binding partner to a molecule on a solid phase. This can, e.g., be the detection of binding of an antibody suspected to be present in a biological sample to or with an antigen, in casu a protein or peptide of the present invention, present on a solid phase. Alternatively, this can be the binding of an HCV nucleic acid suspected to be present in a biological sample to or with an HCV nucleic acid or oligonucleotide of the invention present on a solid phase. In yet another alternative, this can be the binding of an HCV nucleic acid or oligonucleotide of the invention to or with an HCV nucleic acid suspected to be present in a biological sample and immobilized on a solid phase. Automatic development hence refers to a development process, or any one or more steps thereof, in an automated or robotized fashion. A development automate or robot (or, generally, an assay device) generally is connected to or comprises one, more or all of the development or assay reagents and may in addition comprise a means to "read" the developed assay. Said "reading" will logically depend on the assay and may, e.g., confer to determining color intensities, to determining optical density or absorption at a given wavelength, to determining fluoresence, fosforescence or (chemi)luminescence, to determining turbidity, to determining the decay of a radio-active element or to determining other physical or physico-chemical characteristics that are related to the binding of a binding partner in a sample to a molecule present on a solid phase.

The present invention relates furthermore to methods for the detection of nucleic acids of the new HCV clade/genotype of the invention.

A large number of assays capable of detecting nucleotide sequences and nucleotide sequence polymorphisms is currently available. These assays can identify specific mutations, single nucleotide polymorphisms (SNPs), genotype-specific nucleotides or the like. Some of these assays are based on physical methods whereas others use enzymatic approaches.

With "physical detection methods" is meant in the present context methods of nucleotide sequence polymorphism detection that require one or more physical processes for detection although not excluding the enzymatic process of prior PCR amplification of the target DNA sequence comprising one or more nucleotide sequence polymorphisms. Said physical processes include electrophoresis, chromatography, spectrometry, optical signal sensing and spectroscopy. The nucleotide sequence polymorphisms to be detected more specifically are the polymorphisms occurring in the nucleic acids of different HCV genotypes, -subtypes, or -isolates.

Physical nucleotide sequence polymorphism detection assays include electrophoretic methods such as SSCP (single stranded conformation polymorphism), CDCE (constant denaturant capillary electrophoresis), CDGE (constant denaturant gel electrophoresis), DGGE (denaturing gradient gel electrophoresis), TGCE (thermal gradient capillary electrophoresis), DGCE (double gradient capillary electrophoresis), nonisocratic CZE (capillary zone electrophoresis), TDGS (two-dimensional gene scanning), CSGE (conformation sensitive gel electrophoresis), MADGE (microplate array diagonal gele electrophoresis), DSCA (double stand conformation analysis), FIMA (heteroduplex mobility assay), HTA (heteroduplex tracking assay); chromatographic methods include DHPLC (denaturing high performance liquid chromatography). Physical nucleotide sequence polymorphism detection assays may be effective for identification of known or new mutations and may require confirmation by direct DNA sequencing. Probes or primers utilized in any of these physical nucleotide sequence polymorphism detection assays may be modified to increase their discriminatory power, such modifications including the addition of a GC-clamp (i.e., an artificial high-melting domain) to a probe or primer.

MALDI-TOF MS (matrix-assisted laser desorption-ionization time-of-flight mass spectrometry) has been successfully used both as a direct DNA sequencing tool for DNA fragments under 100 bp and as a tool for detection of single nucleotide polymorphisms. Hybridization of allele-specific PNA-oligomers (peptide nucleic acid) with single stranded target DNA was proven to be highly compatible with MALDI-TOF MS analysis (Griffin et al. 2000, and references therein).

With "enzymatic approaches for the generation of products signaling nucleotide sequence polymorphisms" is meant in the present context approaches relying on the activity of one or more enzymes for generation of said signaling products. Enzymes include DNA restriction endonucleases, DNA polymerases, DNA ligases, DNA/RNA structure-specific endonucleases, DNA/RNA flap endonucleases, DNA exonucleases and reverse transcriptases (RTs). Enzymatic approaches usually require a physical process (e.g. as described supra) for detection of the enzymatically produced signal. Said enzymatic approaches include RFLP (restriction fragment length polymorphism), AFLP (amplified fragment length polymorphism), ASO-PCR (allele-specific oligonucleotide PCR), real-time PCR, LCR (ligase chain reaction) and any variation thereof, LDR (ligase detection reaction), CFLP (Cleavase fragment length polymorphism), EMD (enyzmatic mutation detection), NIRCA (non-isotropic RNase cleavage assay), Invader™ assay and its modifications, MIDAS (mutation identification DNA analysis system), ddF (dideoxy fingerprinting), Bi-ddF (bidirectional ddF), dnF (denaturing ddF), BESS (base excision sequence scanning) and DNA minisequencing or DNA sequencing. Probes or primers utilized in any of these enzymatically-based nucleotide sequence polymorphism detection assays may carry specific modifications in order to detect the target nucleotide sequence polymorphism. Such modifications include labeling with a single label, with two different labels (for instance two fluorophores or one fluorophore and one quencher), the attachment of a different 'universal' tail to two probes or primers hybridizing adjacent or in close proximity to each other with the target nucleotide sequence, the incorporation of a target-specific sequence in a hairpin probe or primer (for instance Molecular Beacon-type primer), the tailing of such a hairpin probe or primer with a 'universal' tail (for instance Sunrise-type probe and Amplifluor™-type primer). A special type of hairpin probe/primer incorporates in the hairpin a sequence capable of hybridizing to part of the newly amplified target DNA. Amplification of the hairpin is prevented by the incorporation of a blocking nonamplifiable monomer (such as hexethylene glycol). A fluorescent signal is generated after opening of the hairpin due to hybridization of the hairpin loop with the amplified target DNA. This type of hairpin probe/primer is know as scorpion primers (Whitcombe et al. 1999). Another special type of probe is a padlock probe (or circularizable probe or open circle probe or C-probe) that are used in RCA (rolling circle amplification). The technique of CFLP fingerprinting has already been applied to perform HCV genotyping (Sreevatsan et al. 1998). A chemical alternative for CFLP or NIRCA is the CCM assay (chemical cleavage of mismatch).

DNA sequencing methods include the Maxam and Gilbert protocol, the Sanger reaction (dideoxynucleotide chain termination reaction) and modifications thereof, pyrosequencing, cycle sequencing, SBH (sequencing by hybridization). A variation of the minisequencing procedure is GBA (Genetic Bit Analysis).

Other DNA sequencing methods include molecular resonance sequencing which uses electrospray ionization (ESI) combined with Fourier transform ion cyclotron resonance (FTICR) mass spectrometry (Smith et al., 1994) and, for smaller DNA fragments, MALDI-TOF MS). Diagnostic sequencing by combining specific cleavage of DNA followed by mass spectrometric analysis of the fragments has also been described (see e.g. Stanssens and Zabeau 2000-WO0/66771).

In the near future, nanopore sequencing might also become available (Meller et al., 2000).

For analyzing nucleotide sequence polymorphism in RNA target molecules, both ribozymes (hammerhead-, hairpin-, group I intron-, ribonuclease P- or hepatitis delta viral-type ribozymes) or deoxyribozymes ('DNAzymes') can be used. This feature is moreover the basis for the possible use of these enzymes as therapeutics or in gene therapy (Cairns et al., 2000; James et al., 1995).

The DNA sequencing methodology known as SBH or sequencing-by-hybridization uses an array of all possible n-nucleotide oligomers (n-mers) to identify said n-mers comprised in an unknown DNA sample (Drmanac et al., 1993). Such high-density oligonucleotide arrays are useful for detecting DNA sequence polymorphisms as well, the array eventually becoming a VDA (variant detector array) (Sapolsky et al., 1999; Hacia et al., 1996). Microscope slides can be replaced by optical fibers as solid support for the oligonucleotides (Healey et al. 1997). A variation of the above-described SBH is based on solution hybridization of probes with a known information region or information tags with the target DNA fragments to be sequenced. The information tag can be a DNA bar code (eventually comprising modified bases), a molecular bar code or a nanoparticle bar code and forms the basis for identification and characterization of the hybridized target DNA (Drmanac 2000-WO/0056937). Said high-density oligonucleotide arrays or DNA chips abolish the need to design a set of oligonucleotides specifically hybridizing under the same conditions to a set of polymorphic nucleotide sequences. The latter approach is applied in conventional reverse blot assays by carefully adjusting length, polarity and position of the mismatched nucleotide(s) in the oligonucleotide probe (Saiki et al., 1989). Conventional reverse blot hybridization assays for genotyping and detection of nucleotide sequence polymorphisms have been successfully commercialized, e.g. in the LiPA (Line Probe Assay) format (Innogenetics, Ghent, Belgium). (Stuyver et al., 1997; Stuyver et al., 1996).

Alternatively, Acrydite™-modified oligonucleotide probes are copolymerized into a polyacrylamide gel. Single-stranded target DNA targets are electrophoresed through said gel and, depending on electrophoresis conditions (temperature and/or denaturant), captured by the oligonucleotides immobilized in a capture gel layer. This method is also applicable for detecting nucleotide sequence polymorphisms (Kenney et al., 1998).

Other hybridization-based methods for detecting nucleotide sequence polymorphisms include the solution phase sandwich hybridization assay in which the target DNA is captured by a target-specific immobilized capture probe and detected via an amplifier or linker probe. Two methods of signal generation have been described. A first one utilizes a branched oligonucleotide hybridizing to the flap of the linker probe not binding to the target DNA. Subsequently a labeled probe is hybridized to the branches of the amplifier probe and the amount of bound label is quantified. In a second method, a (partially) double stranded amplifier probe is hybridized to the flap of the linker probe not binding to the target DNA. The double stranded (part of) said amplifier probe comprises a promoter recognized by a DNA-dependent RNA polymerase. The signal generated is formed by newly transcribed RNA from the amplifier probe, the amount of which is quantified. (see e.g. Urdea 1991-WO91/10746).

It will be clear to the skilled person that many variations and combinations can be made to the nucleotide sequence and nucleotide sequence polymorphism detection methods described above. These are hereby incorporated in the present invention.

Based on the above explanation on methods for detecting nucleotide sequences and polymorphisms therein, the following further embodiments are included in the present invention.

The oligonucleotides according to the invention as described supra can be adapted such that they can be used in any of the methods as described above for detection of the HCV nucleotide sequences, or at least one polymorphism or genotype-specific or specific nucleotide therein, according to the invention.

Thus, in an additional embodiment of the present invention, the oligonucleotide according to the invention further comprises a terminal extension and/or a hairpin structure, wherein said extension and/or hairpin structure is incorporated at either end or at both ends of said oligonucleotide. Said terminal extension is useful for, e.g., specifically hybridizing with another nucleic acid molecule (e.g. functioning as capture probe), and/or for facilitating attachment of said oligonucleotide to a solid support, and/or for modification of said tailed oligonucleotide by an enzyme, ribozyme or DNAzyme.

In a further embodiment of the current invention, the oligonucleotide according to the invention is comprised within a padlock probe as described above or within a hairpin structure.

In another embodiment, the oligonucleotide of the present invention has a modification allowing detection and/or capturing of said oligonucleotide. Detection and/or capturing of said oligonucleotide furthermore enables detection and/or capturing of the target nucleic acid hybridized therewith. The interaction between said oligonucleotide and said target nucleic acid may be stabilized by cross-linking both via introduction of a cross-linking modification in said oligonucleotide and/or said target nucleic acid.

In yet another embodiment, the oligonucleotide of the invention comprises a 3'-terminal mismatching nucleotide and, optionally, a 3'-proximal mismatching nucleotide. Said oligonucleotides are particularly useful for performing polymorphism-specific PCR and LCR (or any modification of PCR or LCR).

Further comprised in the present invention is a composition comprising at least one oligonucleotide according to the description given above.

It will be clear to the skilled person that any of the methods described above for detecting nucleotide sequences and polymorphisms therein, such as HCV genotype-specific nucleotides, can be utilized for methods for detecting the presence of an HCV virus in a biological sample; and/or for determining the genotype, i.e. genotyping, of an HCV virus present in a biological sample.

One aspect of the invention relates to a method for detecting the presence of an HCV virus in a biological sample and/or a method for determining the genotype of an HCV virus present in a biological sample, said methods comprising the step of detecting the presence of an HCV nucleic acid or fragment thereof according to the invention.

Said methods can be based on at least one of an amplification reaction, a hybridization reaction, a reverse hybridization reaction or a sequencing reaction. In any of these reactions, an oligonucleotide according to the invention can be utilized. Said methods may further include the use of an oligonucleotide according to the invention for detection of an HCV nucleic acid or fragment thereof of the invention and/or for determining the genotype of the HCV virus present in a biological sample and from which said HCV nucleic acid or fragment was obtained.

A specific embodiment thereto includes said methods comprising the steps of:
(i) obtaining a target HCV nucleic acid from a biological sample suspected to contain an HCV nucleic acid or fragment thereof according to the invention;
(ii) obtaining the nucleic acid sequence of the target HCV nucleic acid of (i);
(iii) inferring, from the nucleic acid sequence obtained in (ii), the presence of an HCV nucleic acid or fragment thereof according to the invention and, therefrom the presence of an HCV in said biological sample and/or the genotype of said HCV virus present in said biological sample.

Another specific embodiment thereto includes said methods comprising:
(i) obtaining a target HCV nucleic acid present in a biological sample and/or obtaining the nucleotide sequence thereof, wherein the biological sample is suspected to contain an HCV virus of the genotype of the invention;
(ii) when appropriate, partial or complete denaturation, or enzymatic modification, of the nucleic acids obtained in step (i);

(iii) when appropriate, renaturation of the denatured polynucleic acids obtained in step (ii), preferably in the presence of at least one oligonucleotide according to the invention, and, if needed, including the step of enzymatically modifying, including extending, said oligonucleotide;

(iv) when appropriate, detection of a discriminatory signal obtained from analysis of the partially or completely denatured nucleic acids obtained in step (ii), and/or of the hybrids formed in step (iii), and/or of the enzymatic modifications obtained in step (ii) and/or (iii);

(v) infering, from the discriminatory signal detected in step (iv), and/or from the nucleotide sequence obtained in (i), the presence of said HCV virus in said biological sample and/or the genotype of said HCV virus present in said biological sample.

In yet another specific embodiment thereto, said methods are comprising:

(i) obtaining a target HCV nucleic acid from a biological sample suspected to contain an HCV nucleic acid or fragment thereof according to the invention;

(ii) contacting the target HCV nucleic acid of (i) with an oligonucleotide of the invention, and said contacting generating a discriminatory signal;

(iii) infering, from the discriminatory signal obtained in (ii), the presence of an HCV nucleic acid or fragment thereof according to the invention and, therefrom, the presence of an HCV virus in said biological sample and/or the genotype of said HCV present in said biological sample.

In the latter methods, said discriminating in (ii) can be based on hybridization and said discriminatory signal in (iii) then is a hybridization signal. Furthermore, the oligonucleotide of the invention can be capable of discriminating at least one genotype-specific or specific nucleotide present in said target HCV nucleic acid or capable of discriminating at least one nucleotide specific to said target HCV nucleic acid.

With an "oligonucleotide capable of discriminating, in a (poly)nucleic acid at least one genotype-specific or specific nucleotide" is meant an oligonucleotide yielding a signal when contacted with a (poly)nucleic acid comprising said at least one genotype-specific or specific nucleotide but not yielding a signal when contacted with a nucleic acid not comprising said at least one genotype-specific or specific nucleotide. Said signal, also referred to as "discriminatory signal", may be any signal obtainable by using said oligonucleotide in any of the assays capable of detecting nucleotide sequences and nucleotide sequence polymorphisms as described above. Said signals include, e.g., fluorescent signals, (chemi)luminescent signals, radioactive signals, light signals, hybridization signals, mass spectrometric signals, spectrometric signals, chromatographic signals, electric signals, electronic signals, electrophoretic signals, real-time PCR signals, PCR signals, LCR signals, CFLP-assay signals and Invader™-assay signals. Said signal implies a sufficiently high signal-to-noise ratio as outlined above.

With "contacting an oligonucleotide with a (poly)nucleic acid" is generally meant annealing of said oligonucleotide with said (poly)nucleic acid or hybridizing said oligonucleotide with said (poly)nucleic acid. "Contacting an oligonucleotide with a (poly)nucleic acid" does not exclude and can thus further comprise enzymatic modification of said oligonucleotide wherein said modification may occur at the extremities of said oligonucleotide and/or internally in the nucleotide sequence of said oligonucleotide. Examples of enzymatic modifications of oligonucleotides are for instance applied in several of the assays capable of detecting nucleotide sequences and nucleotide sequence polymorphisms described herein.

In another embodiment of the invention said methods further comprise, where applicable, aligning and/or comparing the obtained nucleic acid sequence with a set of HCV nucleic acid sequences contained within a database.

With "database" is meant in the present context a collection of nucleic acid or amino acid sequences, more specifically of HCV nucleic acid or amino acid sequences. A database is to be understood to comprise at least one nucleic acid or at least one amino acid sequence. A database can be recorded on a variety of carriers. Such carriers include computer readable carriers.

Comparison of sequences, e.g. determination of percent identity between sequences, and alignment of sequences can be performed using a mathematical algorithm. Determination of percent identity between sequences relies on a previous alignment of sequences. The percentage identity (and similarity) between sequences can be determined by using e.g. the GAP program (part of GCG, Genetics Computer Group, software; now available via Accelrys on http://www.accelrys.com). Alignments between sequences can e.g. be made using the ClustalW algorithm (e.g. part of GCG software or part of VNTI software distributed by InforMax Inc.). An alignment usually is a gapped alignment, i.e. the introduction of gaps in a sequence is allowed in order to optimize the alignment. A detailed statistical theory for gapped alignments has not been developed, and the best gap costs to use with a given substitution matrix are to be determined empirically. These algorithms make use of amino acid substitution matrices to detect similarities among sequences that have diverged (Altschul, 1991). Substitution matrices have also been applied to DNA sequence comparison (States et al., 1991). It will be clear to the one skilled in the art that the efficiency of aligning similar amino acid residues also determines the percentage of identity between sequences. A commonly used substitution matrix is the BLOSUM62 matrix. For particularly long and weak alignments, the BLOSUM45 matrix may be used. For alignment of short sequences, the older PAM (percent accepted mutation)-matrices may be used (e.g. PAM30, PAM70). A good alignment of sequences with a larger evolutionary distance can be to obtained by using a PAM substitution matrix with a greater number (e.g. by using PAM100 instead of PAM40). The number after the BLOSUM matrix (e.g. BLOSUM62) refers to the minimum percent identity of the blocks used to construct the matrix; greater numbers are lesser distances. A database of sequences can be searched against using a nucleic acid or amino acid sequence of interest as 'query sequence'. Algorithms for searching databases are usually based on the BLAST software (Altschul et al., 1990) and comprise: 1) BLASTN, for searching a nucleic acid query sequence against a database of nucleic acid sequences; 2) BLASTP, for searching an amino acid query sequence against a database of amino acid sequences; 3) TBLASTN, for searching a amino acid query sequence against a database of translated nucleic acid sequences (translations in the six possible frames); 3) BLASTX, for searching a translated nucleic acid query sequence (translations in the six possible frames) against a database of amino acid sequences; and 4) TBLASTX, for searching a translated nucleic acid query sequence (translations in the six possible frames) against a database of translated nucleic acid sequences (translations in the six possible frames). For short query sequences, the expect value threshold is preferably set high, e.g. at 1000 for nucleotide sequences and at 20000 for amino acid sequences.

The present invention also relates to a method for the detection of HCV nucleic acids present in a biological sample, comprising:
(i) optionally extracting sample nucleic acid,
(ii) amplifying the nucleic acid with at least one primer as defined herein,
(iii) detecting the amplified nucleic acids.

The present invention also relates to a method for the detection of HCV nucleic acids present in a biological sample, comprising:
(i) optionally extracting sample nucleic acid,
(ii) optionally amplifying the nucleic acid with at least one primer as defined herein, and/or with a universal HCV primer,
(iii) hybridizing the nucleic acids of the biological sample, optionally under denatured conditions, at appropriate conditions with one or more probes as defined herein, with said probes being preferably attached to a solid substrate,
(iv) optionally washing at appropriate conditions,
(v) detecting the hybrids formed.

The present invention in particular relates to a method for the detection of HCV nucleic acids present in a biological sample, comprising:
(i) optionally extracting sample nucleic acid,
(ii) determining the presence of an HCV type nucleic acid sequence according to the invention by means of sequencing of the HCV nucleic acid present in said biological sample.

The present invention also relates to a method for detecting the presence of one or more HCV genotypes present in a biological sample, comprising:
(i) optionally extracting sample nucleic acid,
(ii) specifically amplifying the nucleic acid with at least one primer as defined herein,
(iii) detecting said amplified nucleic acids.
(iv) inferring the presence of one or more HCV genotypes present from the observed pattern of amplified products.

The present invention also relates to a method for detecting the presence of one or more HCV genotypes present in a biological sample, comprising:
(i) optionally extracting sample nucleic acid,
(ii) optionally amplifying the nucleic acid with at least one primer as defined herein and/or with a universal HCV primer,
(iii) hybridizing the nucleic acids of the biological sample, optionally under denatured conditions, at appropriate conditions with one or more probes as defined herein, with said probes being preferably attached to a solid substrate,
(iv) optionally washing at appropriate conditions,
(v) detecting the hybrids formed,
(vi) inferring the presence of one or more HCV genotypes present from the observed hybridization pattern.

The present invention also relates to a method as defined herein, wherein said probes are further characterized as defined herein.

In any of the above methods of the invention, the biological sample is suspected or liable to contain HCV or its nucleic acids.

Another aspect of the current invention relates to a diagnostic kit for detecting the presence of an HCV virus in a biological sample and/or for determining the genotype of an HCV virus present in a biological sample, said kit comprising at least a means for detecting the presence of an HCV nucleic acid according to the invention.

Such diagnostic kits are comprising, e.g. at least one nucleic acid and/or oligonucleotide (probe or primer) according to the invention. Said nucleic acid and/or oligonucleotides may be attached to a solid support. Alternatively, a range of such nucleic acids and/or oligonucleotides are attached or coupled to specific locations on the solid support, e.g., in the form of parallel lines. An exemplary solid support is a membrane.

A specific embodiment thereto includes said diagnostic kit further comprising at least one of:
 a means for obtaining the nucleic acid sequence of a target HCV nucleic acid from a biological sample suspected to contain an HCV nucleic acid or oligonucleotide according to the invention; or
 a means for infering, from the nucleic acid sequence obtained from the target HCV nucleic acid, the presence of a nucleic acid unique to an HCV nucleic acid according to the invention, or the presense of at least one genotype-specific or specific nucleotide therein, and, therefrom, the presence in said biological sample of an HCV and/or the genotype of said HCV.

In another specific embodiment, said diagnostic kit is comprising an oligonucleotide capable of discriminating, in said HCV nucleic acid, at least one genotype-specific or specific nucleotide.

In yet another embodiment, said diagnostic kit is additionally comprising a means for detecting the discriminatory signal obtained by contacting the HCV nucleic acid obtained from a biological sample and the nucleic acid(s) and/or oligonucleotide(s) according to the invention.

Another specific embodiment thereto includes said diagnostic kit comprising or further comprising at least one of:
 a means for obtaining a target HCV nucleic acid present in said biological sample and/or obtaining the nucleotide sequence thereof;
 at least one oligonucleotide primer capable of directing specific amplification of an HCV nucleic acid or fragment thereof according to the present invention;
 an oligonucleotide pair suitable for amplification of a target HCV nucleic acid according to the invention wherein said pair comprises at least one oligonucleotide primer capable of directing specific amplification of an HCV nucleic acid or fragment thereof according to the present invention;
 a means for denaturing nucleic acids;
 at least one oligonucleotide according to the invention;
 an enzyme capable of modifying a double stranded or single stranded nucleic acid molecule;
 a hybridization buffer, or components necessary for producing said buffer;
 a wash solution, or components necessary for producing said solution;
 a means for detecting partially or completely denatured nucleic acids and/or a means for detecting hybrids formed in the preceding hybridization and/or a means for detecting enzymatic modifications of nucleic acids, wherein said means is producing a discriminatory signal;
 a means for attaching an oligonucleotide to a known location on a solid support;
 a means for infering from a detected discriminatory signal, and/or from the obtained nucleotide sequence, the presence of an HCV nucleic acid according to the invention, or the presense of at least one genotype-specific or specific nucleotide therein, and, therefrom, the presence of said HCV virus in said biological sample and/or the genotype of said HCV virus present in said biological sample.

With "a means for infering, from a nucleic acid sequence, the presence of a genotype-specific or specific nucleotide" is meant any technique or method to localize and identify in said nucleic acid sequence said genotype-specific or specific nucleotide. Said means can include a method performed manually, or performed computationally, or performed manually and/or computationally. Said means may include aligning and/or comparing an obtained nucleic acid sequence with a set of nucleic acid sequences contained within a database. Said means may furthermore include the result of the method being presented in the form of a report wherein said report can be in paper form, in electronic form or on a computer readable carrier or medium. Said means may furthermore include the searching of (nucleic acid and/or amino acid) sequence databases and/or the creation of (nucleic acid and/or amino acid) sequence alignments, the results of which may or may not be included in said report. Said means may furthermore include a device for detecting a discriminatory signal, or a kit insert or kit chart indicating how to interpret a detected discriminatory signal, or indicating where a specific discriminatory signal should appear, e.g. on a solid carrier carrying multiple oligonucleotides which can be arranged as spots, lines, dots, etc and possibly interpreting said discriminatory signal occurring on a specific location.

The invention also considers the use of a nucleic acid or oligonucleotide as disclosed herein in a diagnostic method for detecting the presence of an HCV in a biological sample and/or for determining the genotype of said HCV.

The invention also considers the use of a nucleic acid or oligonucleotide as disclosed herein for the manufacture of a diagnostic kit for detecting the presence of an HCV in a biological sample and/or for determining the genotype of said HCV.

The term "nucleic acid" can also be referred to as analyte strand and corresponds to a single- or double-stranded nucleic acid molecule. This analyte strand is preferentially positive- or negative stranded RNA, cDNA or amplified cDNA.

The term "universal HCV primer" refers to oligonucleotide sequences complementary to any of the regions conserved in the HCV genomes of most or all HCV genotypes.

The expression "appropriate hybridization and washing conditions" is to be understood as stringent and are generally known in the art (e.g. Sambrook et al., 1989). However, according to the hybridization solution (SSC, SSPE, etc.), these probes should be hybridized at their appropriate temperature in order to attain sufficient specificity. In order to allow hybridization to occur, the nucleic acid molecules are generally thermally, chemically (e.g. by NaOH) or electrochemically denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and $Na_3$-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (Sambrook et al., 1989) but the skilled craftsman will appreciate that numerous different hybridization conditions can be designed in function of the known or the expected homology and/or length of the nucleic acid sequence. Generally, for hybridizations with DNA probes without formamide, a temperature of 68° C., and for hybridization with formamide, 50% (v/v), a temperature of 42° C. is recommended. For hybridizations with oligonucleotides, the optimal conditions (formamide concentration and/or temperature) depend on the length and base composition of the probe and must be determined individually. In general, optimal hybridization for oligonucleotides of about 10 to 50 bases in length occurs approximately 5° C. below the melting temperature for a given duplex. Incubation at temperatures below the optimum may allow mismatched sequences to hybridize and can therefor result in reduced specificity. When using RNA oligonucleotides with formamide (50% v/v) it is recommend to use a hybridization temperature of 68° C. for detection of target RNA and of 50° C. for detection of target DNA. Alternatively, a high SDS hybridization solution can be utilized (Church et al., 1984). The specificity of hybridization can furthermore be ensured through the presence of a crosslinking moiety on the nucleic acid probe (e.g. Huan et al. 2000-WO00/14281). Said crosslinking moiety enables covalent linking of the nucleic acid probe with the target nucleotide sequence and hence allows stringent washing conditions. Such a crosslinking nucleic acid probe can furthermore comprise another label suitable for detection/quantification of the probe hybridized to the target.

The term "labeled" refers to the use of labeled nucleic acids. This may include the use of labeled nucleotides incorporated during the polymerase step of the amplification such as illustrated by Saiki et al. (1988) or Bej et al. (1990) or labeled primers, or by any other method known to the person skilled in the art.

The process of the invention comprises the steps of contacting any of the probes as defined herein, with one of the following elements:
  either a biological sample in which the nucleic acids are made available for hybridization,
  or the purified nucleic acids contained in the biological sample
  or a single copy derived from the purified nucleic acids,
  or an amplified copy derived from the purified nucleic acids, with said elements or with said probes being attached to a solid substrate.

The expression "inferring the presence of one or more HCV genotypes present from the observed hybridization pattern" refers to the identification of the presence of HCV genomes in the sample by analyzing the pattern of binding of a panel of oligonucleotide probes. Single probes may provide useful information concerning the presence or absence of HCV genomes in a sample. On the other hand, the variation of the HCV genomes is dispersed in nature, so rarely is any one probe able to identify uniquely a specific HCV genome. Rather, the identity of an HCV genotype may be inferred from the pattern of binding of a panel of oligonucleotide probes, which are specific for (different) segments of the different HCV genomes. Depending on the choice of these oligonucleotide probes, each known HCV genotype will correspond to a specific hybridization pattern upon use of a specific combination of probes. Each HCV genotype will also be able to be discriminated from any other HCV genotype amplified with the same primers depending on the choice of the oligonucleotide probes. Comparison of the generated pattern of positively hybridizing probes for a sample containing one or more unknown HCV sequences to a scheme of expected hybridization patterns, allows one to clearly infer the HCV genotypes present in said sample.

The present invention thus relates to a method as defined herein, wherein one or more hybridization probes are oligonucleotide fragments taken from any of SEQ ID NOs:1, 2, 9, 10 or 16 or sequence variants thereof as defined herein. In particular, said oligonucleotide probes hybridize with any of, or at least one of SEQ ID NOs: 1 to 15.

In order to distinguish the amplified target HCV genomes from each other, the amplified target HCV polynucleic acids are hybridized to a set of sequence-specific DNA probes targeting HCV genotype regions (unique regions) located in the HCV polynucleic acids. Most of these probes target the most type- or subtype-specific regions of HCV genotypes, but some can hybridize to more than one HCV genotype. Depending on the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions, i.e. tetraalkylammonium salt solutions (Jacobs et al., 1988). Suitable assay methods for purposes of the present invention to detect hybrids formed between the oligonucleotide probes and the nucleic acid sequences in a sample may comprise any of the assay formats known in the art, such as the conventional dot-blot format, sandwich hybridization or reverse hybridization. For example, the detection can be accomplished using a dot blot format, the unlabelled amplified sample being bound to a membrane, the membrane being incorporated with at least one labeled probe under suitable hybridization and wash conditions, and the presence of bound probe being monitored. An alternative and preferred method is a "reverse" dot-blot format, in which the amplified sequence contains a label. In this format, the unlabelled oligonucleotide probes are bound to a solid support and exposed to the labeled sample under appropriate stringent hybridization and subsequent washing conditions. It is to be understood that also any other assay method which relies on the formation of a hybrid between the nucleic acids of the sample and the oligonucleotide probes according to the present invention may be used.

Probes of the invention can be immobilized in a Line Probe Assay (LiPA) format. This is a reverse hybridization format using membrane strips onto which several oligonucleotide probes (including negative or positive control oligonucleotides) can be conveniently applied as parallel lines. The LiPA is a very rapid and user-friendly hybridization test. Results can be read after 4 hours after the start of the amplification. After amplification during which usually a non-isotopic label is incorporated in the amplified product, and alkaline denaturation, the amplified product is contacted with the probes on the membrane and the hybridization is carried out for about 1 to 1.5 h hybridized polynucleic acid is detected. From the hybridization pattern generated, the HCV type can be deduced either visually, but preferably using dedicated software. The LiPA format is completely compatible with commercially available scanning devices, thus rendering automatic interpretation of the results very reliable. All those advantages make the LiPA format liable for the use of HCV detection in a routine setting. The LiPA format should be particularly advantageous for detecting the presence of different HCV genotypes.

The invention thus also relates to a solid support, preferably a membrane strip, carrying on its surface, one or more probes as defined herein, coupled to the support in the form of parallel lines.

The present invention also relates to a method for detecting and identifying novel HCV genotypes, different from the known HCV genomes, comprising the steps of:
  determining to which HCV genotype the nucleotides present in a biological sample belong, according to a method as defined herein,
  in the case of observing a sample comprising an HCV isolate that is not classifiable as a known HCV genotype determining the sequence of (part of) the genome of the unclassifiable HCV isolate and establishing the relation of the unclassifiable HCV isolate to known HCV clades, -genotypes, -subtypes by means of for instance sequence alignments and/or phylogenetic analysis.

The HCV Core protein, the HCV envelope proteins and HCV non-structural proteins correspond to the HCV polyprotein domains spanning amino acids 1-191 (for Core), 192-383 (for E1), spanning amino acids 384-809 or 384-746 (for E2-p7 and E2, respectively), spanning amino acids 810-1026 (for NS2), spanning amino acids 1027-1657 (for NS3), spanning amino acids 1658-1711 (for NS4A), spanning amino acids 1712-1972 (for NS4B), spanning amino acids 1973-2420 (for NS5A), and spanning amino acids 2421-3011 (for NS5B). It is to be understood that these protein endpoints are approximations (e.g. the carboxy terminal end of E2 could lie somewhere in the 730-820 amino acid region, e.g. ending at amino acid 730, 735, 740, 742, 744, 745, preferably 746, 747, 748, 750, 760, 770, 780, 790, 800, 809, 810, 820). The protein endpoints listed above may also vary depending on genotype-, subtype- or isolate-specific insertions and/or deletions occurring in the HCV genome (see for instance section on Genotype-specific insertions and deletions on page 198 of Maertens and Stuyver, 1997).

The terms peptide, polypeptide and protein are used interchangeably herein.

The term "protein, peptide or polypeptide" is meant to include all protein molecules comprising or consisting of a part of an HCV protein according to the invention. The lower size limit of a protein is a protein comprising or consisting of at least 5 contiguous amino acids of an HCV protein according to the invention. A protein thus can comprise or consist of at least and/or comprise or consist of up to 5, 6, 7, 8, 9, 10, 11, 12, 13, 14, 15, 16, 17, 18, 19, 20, 21, 22, 23, 24, 25, 26, 27, 28, 29, 30, 35, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200 or more contiguous amino acids of an HCV protein according to the invention.

Another aspect of the invention relates to isolated proteins comprising an HCV amino acid sequence encoded by an HCV nucleic acid sequence according to the invention. In a specific embodiment thereto, said isolated protein is defined by an amino acid sequence is defined by SEQ ID NOs:3 or 4. Further included in the present invention are peptides of at least 5 contiguous amino acids taken from an HCV amino acid sequence according to the invention and wherein said peptide comprises at least one amino acid that is different from any HCV amino acid sequence of an HCV of clades 1 to 6 or different from any HCV amino acid sequence of an HCV genotype or subtype of clades 1 to 6. If the HCV amino acid sequence in a protein or peptide of the invention is comprising at least one cysteine, said cysteine can be reversibly or irreversibly protected. Derivatives of a protein or peptide of the invention are also included herein.

A derivative of a protein or part thereof according to the invention is meant to include proteins comprising derivatized amino acids (e.g., conjugated with biotin or digoxigenin), non-natural amino acids, HCV proteins comprising insertions or substitutions (such as conserved substitutions) of one or more amino acids, or HCV proteins wherein one or more amino acids are deleted (all relative to a naturally occurring HCV protein sequence as characterized in the current invention), as well as fusion proteins. A derivatized amino acid includes a derivatized cysteine wherein the derivatization is a modification of the thiol group and/or another modification. Fusion proteins may be formed between two distinct HCV peptides or between an HCV peptide and another peptide or protein such as a B-cell epitope, a T-cell epitope, a CTL epitope or a cytokine. Other peptide or protein fusion partners include bovine serum album, keyhole limpet hemocyanin, soybean or horseradish peroxidase, beta-galactosidase, luciferase, alkaline phosphatase, glutathione S-transferase or dihydrofolate reductase or heterologous epitopes such as (histidine)$_6$-tag, protein A, maltose-binding protein, Tag•100 epitope, c-myc epitope, FLAG®-epitope, lacZ, CMP (calmodulin-binding peptide), HA epitope, protein C epitope or VSV epitope. Other proteins include histones, single-strand binding protein (ssB) and native and engineered fluorescent proteins such as green-, red-, blue-, yellow-, cyan-fluorescent proteins.

More specifically, the polypeptides or fragments thereof according to the invention include recombinant polypeptides, synthetic polypeptides or polypeptides comprising one or more modified or labeled amino acids.

Other protein modifications include polypeptides containing one or more analogues of an amino acid (including, for example, unnatural amino acids, PNA, etc.), polypeptides with substituted linkages, as well as other modifications known in the art, both naturally occurring and non-naturally occurring. Said modifications also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues. A number of said amino acid modifications can occur as a result of post-translational modification as will be recognized by the one skilled in the art. Other modifications include the addition of a chemical group to one or more amino acids of a protein, peptide or oligopeptide. Said chemical groups include e.g. biotin. Said chemical groups further include groups introduced on cysteine-thiols resulting either in a reversibly or irreveribly blocked cysteine-thiol; examples of cysteine-modifying compounds include N-ethylmaleimide, biotin-N-ethylmaleimide, vinylpyridine, iodoacetic acid, iodoacetamide, ethylenimide, and methyliodide. Furthermore, cysteines can be converted into S-sulfo-cysteines in a sulfitolysis reaction. Proteins, peptides or oligopeptides can furthermore generally be labeled radioactively, chemiluminescently, fluorescently, phosphorescently, with infrared dyes or with a surface-enhanced Raman label or plasmon resonant particle. By "biologically equivalent" if used herein, is meant that a protein is an antigenic or immunogenic equivalent to a protein or peptide of the invention.

Any of the proteins, parts thereof or derivatives of any thereof according to the present invention may be of synthetic origin, i.e. synthesized by applying organic chemistry, or of recombinant origin. HCV peptides may be produced by expression in, e.g., mammalian or insect cells infected with recombinant viruses, yeast cells or bacterial cells.

More particularly, said mammalian cells include HeLa cells, Vero cells, RK13 cells, MRC-5 cells, Chinese hamster ovary (CHO) cells, Baby hamster kidney (BHK) cells and PKI5 cells. More particularly, said insect cells include cells of *Spodoptera frugiperda*, such as Sf9 cells. More particularly, said recombinant viruses include recombinant vaccinia viruses, recombinant adenoviruses, recombinant baculoviruses, recombinant canary pox viruses, recombinant Semliki Forest viruses, recombinant alphaviruses, recombinant Ankara Modified viruses and recombinant avipox viruses. More particularly, said yeast cells include cells of *Saccharomyces*, such as *Saccharomyces cerevisiae, Saccharomyces kluyveri*, or *Saccharomyces uvarum, Schizosaccharomyces*, such as *Schizosaccharomyces pombe, Kluyveromyces*, such as *Kluyveromyces lactis, Yarrowia*, such as *Yarrowia lipolytica, Hansenula*, such as *Hansenula polymorpha, Pichia*, such as *Pichia pastoris, Aspergillus* species, *Neurospora*, such as *Neurospora crassa*, or *Schwanniomyces*, such as *Schwanniomyces occidentalis*, or mutant cells derived from any thereof. More specifically, the HCV peptide or part thereof according to the invention is the product of expression in a *Hansenula* cell. More particularly, said bacterial cells include cells of *Escherichia coli* or *Streptomyces* species.

In the protein, part thereof or derivative of any thereof according to the invention and comprising at least one cysteine residue, the cysteine thiol-group(s) can be irreversibly protected by chemical means. "Irreversible protection" or "irreversible blocking" by chemical means refers to alkylation by means of alkylating agents, such as, for example, active halogens, ethylenimine or N-(iodoethyl)trifluoro-acetamide. In this respect, it is to be understood that alkylation of cysteine thiol-groups refers to the replacement of the thiol-hydrogen by $(CH_2)_nR$, in which n is 0, 1, 2, 3 or 4 and R=H, COOH, $NH_2$, $CONH_2$, phenyl, or any derivative thereof. Alkylation can be performed by any method known in the art, such as, for example, active halogens $X(CH_2)_nR$ in which X is a halogen such as I, Br, Cl or F. Examples of active halogens are methyliodide, iodoacetic acid, iodoacetamide, and 2-bromoethylamine. Other methods of alkylation include the use of NEM (N-ethylmaleimide) or Biotin-NEM, a mixture thereof, or ethylenimine or N-(iodoethyl)trifluoroacetamide both resulting in substitution of —H by —$CH_2$—$CH_2$—$NH_2$ (Hermanson 1996). The term "alkylating agents" as used herein refers to compounds which are able to perform alkylation as described herein.

It is further understood that the cysteine thiol-groups of the HCV proteins or the parts thereof or the derivatives of any thereof of the present invention can be reversibly protected. The purpose of reversible protection is to stabilize the HCV protein or part thereof or derivative of any thereof. Especially, after reversible protection the sulfur-containing functional group (e.g. thiols and disulfides) is retained in a non-reactive condition. The sulfur-containing functional group is thus unable to react with other compounds, e.g. have lost their tendency of forming or exchanging disulfide bonds, such as, for example

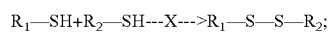

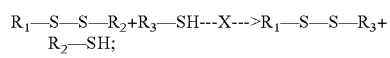

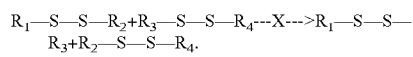

The described reactions between thiols and/or disulfide residues are not limited to intermolecular processes, but may also occur intramolecularly.

The term "reversible protection" or "reversible blocking" as used herein contemplates covalently binding of modification agents to the cysteine thiol-groups, as well as manipulating the environment of the HCV protein such, that the redox state of the cysteine thiol-groups remains unaffected throughout subsequent steps of the purification procedure (shielding). Reversible protection of the cysteine thiol-groups can be carried out chemically or enzymatically.

The term "reversible protection by enzymatical means" as used herein contemplates reversible protection mediated by enzymes, such as for example acyl-transferases, e.g. acyl-transferases that are involved in catalysing thio-esterification, such as palmitoyl acyltransferase (see below).

The term "reversible protection by chemical means" as used herein contemplates reversible protection:

1. by modification agents that reversibly modify cysteinyls such as for example by sulfonation and thio-esterification;
   Sulfonation is a reaction where thiol or cysteines involved in disulfide bridges are modified to S-sulfonate: RSH□ RS—$SO_3^-$ (Darbre 1986) or RS—SR□ 2 RS—$SO_3$- (sulfitolysis; Kumar et al. 1986). Reagents for sulfonation are e.g. $Na_2SO_3$, or sodium tetrathionate. The latter reagents for sulfonation are used in a concentration of 10-200 mM, and more preferentially in a concentration of 50-200 mM. Optionally sulfonation can be performed in the presence of a catalysator such as, for example $Cu^{2+}$ (100 μM-1 mM) or cysteine (1-10 mM).
   The reaction can be performed under protein denaturing as well as native conditions (Kumar et al. 1985, Kumar et al. 1986).
   Thioester bond formation, or thio-esterification is characterised by:

RSH+R'COX□RS—COR' in which X is preferentially a halogenide in the compound R'CO—X.
2. by modification agents that reversibly modify the cysteinyls of the present invention such as, for example, by heavy metals, in particular $Zn^{2+}$, $Cd^{2+}$, mono-, dithio- and disulfide-compounds (e.g. aryl- and alkylmethanethiosulfonate, dithiopyridine, dithiomorpholine, dihydrolipoamide, Ellmann reagent, Aldrothiol™ (Aldrich) (Rein et al. 1996), dithiocarbamates), or thiolation agents (e.g. gluthathion, N-Acetyl cysteine, cysteineamine). Dithiocarbamate comprise a broad class of molecules possessing an $R_1R_2NC(S)SR_3$ functional group, which gives them the ability to react with sulfydryl groups. Thiol containing compounds are preferentially used in a concentration of 0.1-50 mM, more preferentially in a concentration of 1-50 mM, and even more preferentially in a concentration of 10-50 mM;
3. by the presence of modification agents that preserve the thiol status (stabilise), in particular antioxidantia, such as for example DTT, dihydroascorbate, vitamins and derivates, mannitol, amino acids, peptides and derivates (e.g. histidine, ergothioneine, carnosine, methionine), gallates, hydroxyanisole, hydoxytoluene, hydroquinon, hydroxymethylphenol and their derivates in concentration range of 10 μM-10 mM, more preferentially in a concentration of 1-10 mM;
4. by thiol stabilising conditions such as, for example, (i) cofactors as metal ions ($Zn^{2+}$, $Mg^{2+}$), ATP, (ii) pH control (e.g. for proteins in most cases pH ~5 or pH is preferentially thiol $pK_a$ −2; e.g. for peptides purified by Reversed Phase Chromatography at pH ~2).

Combinations of reversible protection as described in (1), (2), (3) and (4) may result in similarly pure and refolded HCV proteins. In effect, combination compounds can be used, such as, for example Z103 (Zn carnosine), preferentially in a concentration of 1-10 mM. It should be clear that reversible protection also refers to, besides the modification groups or shielding described above, any cysteinyl protection method which may be reversed enzymatically or chemically, without disrupting the peptide backbone. In this respect, the present invention specifically refers to peptides prepared by classical chemical synthesis (see above), in which, for example, thioester bounds are cleaved by thioesterase, basic buffer conditions (Beekman et al. 1997) or by hydroxylamine treatment (Vingerhoeds et al. 1996).

Reversible protection may also be used to increase the solubilisation and extraction of peptides (Pomroy and Deber 1998).

The reversible protection and thiol stabilizing compounds may be presented under a monomeric, polymeric or liposomic form.

The removal of the reversibly protection state of the cysteine residues can chemically or enzymatically accomplished by e.g.:

- a reductant, in particular DTT, DTE, 2-mercaptoethanol, dithionite, $SnCl_2$, sodium borohydride, hydroxylamine, TCEP, in particular in a concentration of 1-200 mM, more preferentially in a concentration of 50-200 mM;
- removal of the thiol stabilising conditions or agents by e.g. pH increase;
- enzymes, in particular thioesterases, glutaredoxine, thioredoxine, in particular in a concentration of 0.01-5 μM, even more particular in a concentration range of 0.1-5 μM.;
- combinations of the above described chemical and/or enzymatical conditions.

The removal of the reversibly protection state of the cysteine residues can be carried out in vitro or in vivo, e.g. in a cell or in an individual.

It will be appreciated that in the purification procedure, the cysteine residues may or may not be irreversibly blocked, or replaced by any reversible modification agent, as listed above. Reversibly blocked cysteines in a protein may be converted to irreversibly blocked cysteines.

A reductant according to the present invention is any agent which achieves reduction of the sulfur in cysteine residues, e.g. "S—S" disulfide bridges, desulfonation of the cysteine residue (RS—$SO_3^-$□RSH). An antioxidant is any reagent which preserves the thiol status or minimises "S—S" formation and/or exchanges. Reduction of the "S—S" disulfide bridges is a chemical reaction whereby the disulfides are reduced to thiol (—SH). "S—S" Reduction can be obtained by (1) enzymatic cascade pathways or by (2) reducing compounds. Enzymes like thioredoxin, glutaredoxin are known to be involved in the in vivo reduction of disulfides and have also been shown to be effective in reducing "S—S" bridges in vitro. Disulfide bonds are rapidly cleaved by reduced thioredoxin at pH 7.0, with an apparent second order rate that is around $10^4$ times larger than the corresponding rate constant for the reaction with DTT. The reduction kinetic can be dramatically increased by preincubation the protein solution with 1 mM DTT or dihydrolipoamide (Holmgren 1979). Thiol compounds able to reduce protein disulfide bridges are for instance Dithiothreitol (DTT), Dithioerythritol (DTE), β-mercaptoethanol, thiocarbamates, bis(2-mercaptoethyl) sulfone and N,N'-bis(mercaptoacetyl)hydrazine, and sodium-dithionite. Reducing agents without thiol groups like ascorbate or stannous chloride ($SnCl_2$), which have been shown to be very useful in the reduction of disulfide bridges in monoclonal antibodies (Thakur et al. 1991), may also be used for the reduction of HCV proteins. In addition, changes in pH values may influence the redox status of HCV proteins. Sodium borohydride treatment has been shown to be effective for the reduction of disulfide bridges in peptides (Gailit 1993). Tris (2-carboxyethyl)phosphine (TCEP) is able to reduce disulfides at low pH (Burns et al. 1991). Selenol catalyses the reduction of disulfide to thiols when DTT or sodium borohydride is used as reductant. Selenocysteamine, a commercially available diselenide, was used as precursor of the catalyst (Singh and Kats 1995).

Another aspect of the current invention relates to the use of an isolated HCV protein or part thereof or derivative of any thereof according to the invention in immunoassays, to the use of an isolated HCV protein or part thereof or derivative of any thereof according to the invention for incorporation in immunoassay kits or diagnostic kits, and to the use of an isolated HCV protein or part thereof or derivative of any thereof according to the invention for the manufacture of a an immunoassay kit or diagnostic kit. Immunoassays comprise immunological methods for determining the presence of antibodies to HCV in a biological sample or of antigens of HCV in a biological sample or of HCV virus in a biological sample, or for diagnosing HCV infection. Diagnostic kits or immunoassay kits comprise kits for determining the presence of antibodies to HCV in a biological sample or of antigens of HCV in a biological sample or of HCV virus in a biological sample, or for diagnosing HCV infection.

In particular said biological sample is suspected to contain HCV antibodies, HCV antigens or HCV virus.

A first general embodiment in relation to immunoassays comprises a method for determining the presence of antibodies to HCV in a biological sample comprising the step of detecting said antibodies with an HCV protein or part thereof or derivative of any thereof according to the invention.

A second general embodiment in relation to immunoassays comprises a method for determining the presence of HCV antigens in a biological sample comprising the step of detecting said HCV antigens with an antibody to said HCV antigens in the presence of an isolated HCV protein or part thereof or derivative of any thereof according to the invention as competitor of binding of said HCV antigens to said antibody.

In particular said immunoassays are relying on an isolated HCV protein or part thereof or derivative of any thereof according to the invention wherein, if said HCV protein or part thereof is comprising at least one cysteine amino acid, said at least one cysteine is reversibly or irreversibly modified. When said at least one cysteine is reversibly modified, the immunoassay may be performed in the absence or presence of a reducing agent.

A first specific embodiment in relation to immunoassays comprises a method for determining the presence of antibodies to HCV, in particular to an HCV protein or part thereof according to the invention, in a biological sample comprising the steps of:
(i) contacting said biological sample with an isolated protein or part thereof or derivative of any thereof according to the invention;
(ii) detecting the immunological complex formed in (i) between said antibodies and said protein or part thereof or derivative of any thereof.

A second specific embodiment in relation to immunoassays comprises a method for determining the presence of an HCV virus in a biological sample comprising the steps of:
(i) contacting said biological sample with an isolated protein or part thereof or derivative of any thereof according to the invention;
(ii) detecting the immunological complex formed in (i) between antibodies to said HCV virus present in said sample and said protein or part thereof or derivative of any thereof,
(iii) inferring from the immunological complex formed in (ii) the presence of an HCV virus in said biological sample.

A third specific embodiment in relation to immunoassays comprises a method for diagnosing HCV infection in a mammal comprising the steps of:
(i) contacting a biological sample from said mammal with an isolated protein or part thereof or derivative of any thereof according to the invention;
(ii) detecting the immunological complex formed in (i) between antibodies to HCV present in said sample and said protein or part thereof or derivative of any thereof;
(iii) diagnosing from the immunological complex formed in (ii) HCV infection in said mammal.

A forth specific embodiment in relation to immunoassays comprises a method for determining the presence of an HCV antigen in a biological sample comprising the steps of:
(i) contacting said biological sample with an antibody to said HCV antigen in the presence of an isolated protein or part thereof or derivative of any thereof according to the invention as competitor, i.e. as competitor of binding of said HCV antigen to said antibody;
(ii) inferring from the immunological complex formed in (i) between said antibody and said HCV antigen the presence of said HCV antigen.

A fifth specific embodiment in relation to immunoassays comprises a method for determining the presence of an HCV virus in a biological sample comprising the steps of:
(i) contacting said biological sample with an antibody to an HCV antigen in the presence of an isolated protein or part thereof or derivative of any thereof according to the invention as competitor;
(ii) detecting the immunological complex formed in (i) between said antibody and said HCV antigen;
(iii) inferring from the immunological complex detected in (ii) the presence of an HCV virus in said biological sample.

A sixth specific embodiment in relation to immunoassays comprises a method for diagnosing HCV infection in a mammal comprising the steps of:
(i) contacting a biological sample from said mammal with an antibody to an HCV antigen in the presence of an isolated protein or part thereof or derivative of any thereof according to the invention as competitor;
(ii) detecting the immunological complex formed in (i) between said antibody and said HCV antigen;
(iii) diagnosing from the immunological complex detected in (ii) HCV infection in said mammal.

The current invention also relates to a method for typing of an HCV virus present in a biological sample comprising the steps of:
(i) contacting said biological sample with a protein or peptide according to the invention;
(ii) detecting the immunological complex formed in (i) between the antibodies to HCV present in said biological sample and said protein or peptide;
(iii) inferring from the immunological complex detected in (ii) the type of HCV virus present in said biological sample.

Said antigen-antibody contacting in the above-described immunoassays is normally performed under conditions allowing the formation of an immunological complex between said antigen and said antibody.

A further embodiment relates to the use of a protein or part thereof or derivative of any thereof according to the invention in an immunoassay.

A further embodiment relates to a diagnostic kit for determining the presence of antibodies to HCV (in particular antibodies to an isolated HCV protein or part thereof according to the invention) in a biological sample, for determining the presence of HCV antigens in a biological sample, for determining the presence of an HCV virus in a biological sample or for diagnosing HCV infection in a mammal, said kit comprising at least one isolated protein or part thereof or derivative of any thereof according to the invention.

The proteins or parts thereof or derivatives of any thereof according to the present invention may be employed in virtually any immunoassay format that employs a known antigen to detect antibodies or a known antibody to detect antigens. A common feature of all of these assays is that the antigen is contacted with the body component containing or suspected of containing HCV antibodies or HCV antigens under conditions that permit binding between an antigen and an antibody, i.e. under conditions allowing the formation of an immunological complex. Such conditions will typically be physiologic temperature, pH and ionic strength using an excess of antigen (in the case of antibody detection) or antibody (in the case of antigen detection). The incubation of the antigen or antibody with the specimen is followed by detection of immune complexes.

The design of immunoassays is subject to a great deal of variation, and many formats are known in the art. Protocols may, for example, use solid supports, or immunoprecipitation. Most assays involve the use of labeled antibody and/or labeled polypeptide, e.g. a labeled peptide or polypeptide according to the present invention; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA and RIA assays. Other immunoassay designs comprise line immunoassays, sandwich immunoassays, antigen down immunoassays. An immunoassay may be set up in a competitive format.

An immunoassay may be, without limitation, in a heterogeneous or in a homogeneous format, and of a standard or competitive type. In a heterogeneous format, the polypeptide is typically bound to a solid matrix, solid support or solid phase to facilitate separation of the sample from the polypeptide after incubation. Examples of solid supports, matrices or phases are listed above. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes that are formed. Both standard and competitive formats for these assays are known in the art.

In a standard format, the amount of antibodies, such as anti-HCV antibodies, in the antibody-antigen complexes is directly monitored. This may be accomplished by determining whether labeled anti-xenogeneic (e.g. anti-human) antibodies which recognize an epitope on said antibodies, such as said anti-HCV antibodies, will bind due to complex formation. In a competitive format, the amount of said antibodies, such as said anti-HCV antibodies, in a sample is deduced by monitoring the competitive effect on the binding of a known amount of (labeled) antibody (or other competing ligand) or antigen in the complex.

Antigen-antibody complexes can be detected by any of a number of known techniques, depending on the format. For example, unlabeled antibodies such as anti-HCV antibodies in the complex may be detected using a conjugate of anti-xenogeneic Ig complexed with a label (e.g. an enzyme label).

In an immunoprecipitation or agglutination assay format the reaction between an antigen and an antibody forms a protein cluster that precipitates from the solution or suspension and forms a visible layer or film of precipitate. If no antibody is present in the test specimen or sample, no such precipitate is formed.

A diagnostic kit usually comprises a molecule for detecting the presence of a sample reactant capable of interacting with said molecule, of a sample reactant modifying said molecule (e.g., in a chemical reaction), and/or of a sample reactant modifiable by said molecule (e.g., in a chemical reaction). In a diagnostic kit for detection of an antigen or antibody in a sample, one or more antibodies or antigens, respectively, are part of said kit. In a diagnostic kit for detecting antigens or antibodies, antibodies or antigens, respectively, are often present on a solid phase, matrix or support.

The proteins or parts thereof or derivatives of any thereof according to the present invention can be packaged and be part of a diagnostic kit. The kit will normally contain in separate containers or vials the peptides or polypeptides according to the present invention (labelled or unlabelled), control antibody formulations (positive and/or negative), labelled antibody when the assay format requires the same and signal generating reagents (e.g. enzyme substrate) if the label does not generate a signal directly. The peptides or polypeptides according to the present invention may be already bound to a solid matrix or may be present in the kit in a separate vial together with reagents for binding it to the matrix. Instructions (e.g. written, tape, CD-ROM, etc.) for carrying out the assay usually will be included in the kit.

The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin. In order to block the effects of rheumatoid factor-like substances, the test sample is subjected to conditions sufficient to block the effect of rheumatoid factor-like substances. These conditions comprise contacting the test sample with a quantity of anti-human IgG to form a mixture, and incubating the mixture for a time and under conditions sufficient to form a reaction mixture product substantially free of rheumatoid factor-like substance.

Diagnostic kits for detecting antibodies to an HCV virus or for typing of an HCV virus wherein said kits comprise at least one protein or peptide according to the invention are part of the invention. In said diagnostic kit said protein or peptide can be bound to a solid support.

The invention further relates to methods for detecting antibodies to an HCV virus present in a biological sample comprising contacting an antigen with said antibodies in the presence of an isolated antibody according to the invention as competitor of binding of said antigen to said antibody.

Another method of the invention is detecting the presence of HCV antigens in a biological sample comprising contacting said antigen with an antibody to said antigen in the presence of an isolated protein or peptide according to the invention as competitor of binding of said antigen to said antibody.

In another aspect, the current invention envisages recombinant vectors comprising a nucleic acid or oligonucleotide according to the invention. More specifically, said recombinant vector can be an expression vector capable of directing expression of an HCV protein encoded by the HCV nucleic acid sequence comprised in said vector.

Host cells transformed with a nucleic acid or oligonucleotide according to the invention or transformed with a recombinant vector according to the invention are also part of the present invention.

A further aspect of the invention relates to a method for the recombinant production of a protein or peptide according to the invention comprising the steps of:
(i) transformation of an appropriate cellular host with a recombinant vector according to the invention;
(ii) culturing the transformed cellular host of (i) under conditions enabling the expression of said protein;
(iii) harvesting the protein expressed in (ii).

In particular the expression of the HCV protein by means of the expression vector will be driven by transcription regulatory elements that are operably linked to the nucleic acid sequence encoding said HCV protein.

As used herein, the term "transcription regulatory elements" refers to a nucleotide sequence which contains essential regulatory elements, such that upon introduction into a living vertebrate cell it is able to direct the cellular machinery to produce transcription products encoded by the polynucleotide. Transcription regulatory elements include promoters, terminators, enhancers, etc.

The term "operably linked" refers to a juxtaposition wherein the components are configured so as to perform their usual function. Thus, transcription regulatory elements operably linked to a nucleotide sequence are capable of effecting the transcription of said nucleotide sequence. Those skilled in the art can appreciate that different transcriptional promoters, terminators, carrier vectors or specific gene sequences may be used successfully.

Host cells for expression of the HCV protein according to the invention can be prokaryotic or eukaryotic cells as described above.

The invention further relates to the use of a recombinant vector according to the invention for the manufacture of an immunogenic composition or a vaccine composition. In particular the immunogenic composition is an HCV immunogenic composition and the vaccine composition is an HCV vaccine composition, a therapeutic HCV vaccine composition or a prophylactic HCV vaccine composition. Any of these compositions can be used for immunizing a mammal against HCV infection or for treating a mammal infected with HCV.

An "immunogenic composition" is a composition comprising an antigen capable of eliciting at least one element of the immune response against the antigen comprised in said composition when said composition is introduced into the body of an animal capable of raising an immune response. An immunogenic composition may comprise more than one antigen, i.e., a plurality of antigens, e.g. 2, 3, 4, 5, 6, 7, 8, 9, 10 or more, e.g., up to 15, 20, 25, 30, 40 or 50 or more distinct antigens. In particular, the immunogenic composition of the invention is an HCV immunogenic composition wherein the antigen or plurality of antigens are peptide(s) or polypeptide(s) or protein(s) or part or derivative of any thereof according to the invention. Said plurality of antigens may comprise a combination of HCV proteins or parts thereof or derivatives of any thereof derived from different HCV genotypes and/or subtypes and/or isolates including the HCV isolates of the new HCV clade/genotype identified in the present invention.

A "vaccine composition" is an immunogenic composition capable of eliciting an immune response sufficiently broad and vigorous to provoke one or both of:
a stabilizing effect on the multiplication of a pathogen already present in a host and against which the vaccine composition is targeted; and
an effect increasing the rate at which a pathogen newly introduced in a host, after immunization with a vaccine composition targeted against said pathogen, is resolved from said host.

A vaccine composition may also provoke an immune response broad and strong enough to exert a negative effect on the survival of a pathogen already present in a host or broad and strong enough to prevent an immunized host from developing disease symptoms caused by a newly introduced pathogen. In particular the vaccine composition of the invention is an HCV vaccine composition wherein the pathogen is HCV.

An "effective amount" of an antigen in a vaccine composition is referred to as an amount of antigen required and sufficient to elicit an immune response. It will be clear to the skilled artisan that the immune response sufficiently broad and vigorous to provoke the effects envisaged by the vaccine composition may require successive (in time) immunizations with the vaccine composition as part of a vaccination scheme or vaccination schedule. The "effective amount" may vary depending on the health and physical condition of the individual to be treated, the taxonomic group of the individual to be treated (e.g. human, non-human primate, primate, etc.), the capacity of the individual's immune system to mount an effective immune response, the degree of protection desired, the formulation of the vaccine, the treating doctor's assessment, the strain of the infecting pathogen and other relevant factors. It is expected that the amount will fall in a relatively broad range that can be determined through routine trials. Usually, the amount will vary from 0.01 to 1000 µg/dose, more particularly from 0.1 to 100 µg/dose. Dosage treatment may be a single dose schedule or a multiple dose schedule. The vaccine may be administered in conjunction with other immunoregulatory agents.

A "prophylactic vaccine composition" is a vaccine composition providing protective immunity, i.e., an immunity preventing development of disease upon challenge of the host immunized with the prophylactic vaccine composition. In particular for HCV, a prophylactic HCV vaccine composition is to be understood as a vaccine composition capable of providing protective immunity helping to resolve a challenge HCV infection rapidly and/or preventing a challenge HCV infection to proceed to a chronic infection. Accelerated HCV viral clearance or accelerated control of HCV challenge infection is thus envisaged by vaccination with a prophylactic HCV composition according to the invention.

A "prophylactically effective amount" of an antigen in a prophylactic vaccine composition is referred to as an amount of antigen required and sufficient to elicit an immune response enabling the development of protective immunity. It will be clear to the skilled artisan that the immune response sufficiently broad and vigorous to provoke the effects envisaged by the prophylactic vaccine composition may need require successive (in time) immunizations with the prophylactic vaccine composition (see also "effective amount").

A "therapeutic vaccine composition" is a vaccine composition providing a curative immune response, i.e., an immune response capable of effectuating a reversion, or at least capable of effectuating halting, of disease symptoms associated with an already established pathogen infection. In particular for HCV, a therapeutic HCV vaccine composition is to be understood as a vaccine compositions capable of reducing serum liver enzyme, e.g., alanine aminotransferase (ALT) or γ-glutamylpeptidase (γ-GT), activity levels in the blood and/or of reducing HCV RNA levels and/or of reducing liver disease and/or of reducing liver fibrosis and/or of reducing liver fibrosis progression and/or reducing HCV antigen levels in or presented on liver cells.

A "therapeutically effective amount" of an antigen in a therapeutic vaccine composition is referred to as an amount of antigen required and sufficient to elicit an immune response enabling the development of a curative immune response. It will be clear to the skilled artisan that the antigenic or immunogenic response sufficiently broad and vigorous to provoke the effects envisaged by the therapeutic vaccine composition may need require successive (in time) immunizations with the therapeutic vaccine composition (see also "effective amount").

Another aspect of the invention relates to compositions, immunogenic compositions and/or vaccine compositions comprising at least one of an nucleic acid or oligonucleotide according to the invention, an isolated protein or peptide according to the invention, a recombinant vector according to the invention or an antibody according to the invention; and at least one of a suitable carrier, adjuvant or vehicle. In particular said immunogenic compositions are HCV immunogenic compositions and said vaccine compositions are HCV vaccine compositions, therapeutic HCV vaccine compositions or prophylactic HCV vaccine compositions. Any of these compositions can be used for immunizing a mammal against HCV infection or for treating a mammal infected with HCV.

The invention relates in a further aspect to HCV immunogenic compositions, HCV vaccine compositions, prophylactic HCV vaccine compositions and/or therapeutic HCV vaccine compositions comprising a protein or part or a derivative of any thereof as described herein.

Another aspect of the current invention relates to the use of an isolated (HCV) protein or part thereof or derivative of any thereof according to the invention for the manufacture of an HCV immunogenic composition, a prophylactic HCV vaccine composition or a therapeutic HCV vaccine composition.

Other aspects of the invention relate to methods of vaccinating an HCV-naïve or HCV-infected mammal comprising administering an HCV immunogenic composition, an HCV vaccine composition, a prophylactic HCV vaccine composition and/or a therapeutic HCV vaccine composition according to the invention in combination with (i.e., before, after or concurrently with) administering a DNA vaccine.

The immunogenic composition, vaccine composition, therapeutic vaccine composition or prophylactic vaccine composition as described above may in addition comprise DNA vaccine vectors capable of expressing or effectuating expression of an antigen. Particularly relating to the current invention, the HCV immunogenic composition, HCV vaccine composition, therapeutic HCV vaccine composition or prophylactic HCV vaccine composition may in addition comprise DNA vaccine vectors capable of expressing or effectuating expression of one or more antigens such as HCV proteins or parts thereof, e.g., an HCV protein or part thereof according to the invention. Alternatively, the protein- or peptide-based immunogenic composition, vaccine composition, therapeutic vaccine composition or prophylactic vaccine composition of the invention may be used in combination with a DNA vector-based immunogenic composition, vaccine composition, therapeutic vaccine composition or prophylactic vaccine composition (also referred to as "DNA vaccine" or "HCV DNA vaccine" if the DNA vector comprised therein is encoding an HCV protein or part thereof). Such combination for instance includes a DNA-prime protein-boost vaccination scheme wherein vaccination is initiated by administering a DNA vector-based immunogenic composition, vaccine composition, therapeutic vaccine composition or prophylactic vaccine composition and is followed by administering a protein- or peptide-based immunogenic composition, vaccine composition, therapeutic vaccine composition or prophylactic vaccine composition of the invention. In particular the DNA vaccine vector is capable of expressing one or more HCV antigens or proteins or parts thereof.

With a "DNA vector" or "DNA vaccine vector" is meant any DNA carrier comprising the open reading frame for one or more of the peptides useful for eliciting and/or enhancing an immune response. In general, said open reading frames are operably linked to transcription regulatory elements, such as promoters and terminators, enabling expression of the peptide encoded by the open reading frame. The terms "DNA vector" or "DNA vaccine vector" are meant to include naked plasmid DNA, plasmid DNA formulated with a suitable pharmaceutically acceptable carrier, adjuvant or vehicle, recombinant viruses (e.g., as described above), or recombinant viruses formulated with a suitable pharmaceutically acceptable carrier, adjuvant or vehicle. A "HCV DNA vector" or "HCV DNA vaccine vector" relates to any DNA carrier comprising an (HCV) nucleic acid or oligonucleotide according to the invention and capable of directing expression of one or more of the (HCV) proteins or peptides of the invention.

The invention relates also to the use of an (HCV) nucleic acid or oligonucleotide according to the invention for the manufacture of an immunogenic composition or a vaccine composition.

In particular the immunogenic composition is an HCV immunogenic composition and the vaccine composition is an HCV vaccine composition, a therapeutic HCV vaccine composition or a prophylactic HCV vaccine composition. Any of these compositions can be used for immunizing a mammal against HCV infection or for treating a mammal infected with HCV.

A "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvantia typically comprise one or more of the compounds included in the following non-exhaustive list:

large slowly metabolized macromolecules such as proteins, polysaccharides, polylactic acids, polyglycolic acids, polymeric amino acids, amino acid copolymers and inactive virus particles;

aluminium hydroxide, aluminium phosphate (see International Patent Application Publication No. WO93/24148), alum ($KAl(SO_4)_2.12H_2O$), or one of these in combination with 3-O-deacylated monophosphoryl lipid A (see International Patent Application Publication No. WO93/19780);

N-acetyl-muramyl-L-threonyl-D-isoglutamine (see U.S. Pat. No. 4,606,918), N-acetyl-normuramyl-L-alanyl-D-isoglutamine, N-acetylmuramyl-L-alanyl-D-isoglutamyl-L-alanine2-(1',2'-dipalmitoyl-sn-glycero-3-hydroxyphosphoryloxy) ethylamine;

RIBI (ImmunoChem Research Inc., Hamilton, Mont., USA) which contains monophosphoryl lipid A (i.e., a detoxified endotoxin), trehalose-6,6-dimycolate, and cell wall skeleton (MPL+TDM+CWS) in a 2% squalene/Tween 80 emulsion. Any of the three components MPL, TDM or CWS may also be used alone or combined 2 by 2. The MPL may also be replaced by its synthetic analogue referred to as RC-529 or by any other amino-alkyl glucosaminide 4-phosphate (Johnson et al. 1999, Persing et al. 2002);

adjuvants such as Stimulon (Cambridge Bioscience, Worcester, Mass., USA), SAF-1 (Syntex);

bacterial DNA-based adjuvants such as ISS (Dynavax) or CpG (Coley Pharmaceuticals);

adjuvants such as combinations between QS21 and 3-de-O-acetylated monophosphoryl lipid A (see International Patent Application Publication No. WO94/00153) which may be further supplemented with an oil-in-water emulsion (see, e.g., International Patent Application Publication Nos. WO95/17210, WO97/01640 and WO9856414) in which the oil-in-water emulsion comprises a metabolisable oil and a saponin, or a metabolisable oil, a saponin, and a sterol, or which may be further supplemented with a cytokine (see International Patent Application Publication No. WO98/57659);

adjuvants such as MF-59 (Chiron), or poly[di(carboxylatophenoxy) phosphazene] based adjuvants (Virus Research Institute);

blockcopolymer based adjuvants such as Optivax (Vaxcel, Cytrx) or inulin-based adjuvants, such as Algammulin and GammaInulin (Anutech);

Complete or Incomplete Freund's Adjuvant (CFA or IFA, respectively) or Gerbu preparations (Gerbu Biotechnik). It is to be understood that Complete Freund's Adjuvant (CFA) may be used for non-human applications and research purposes as well;

a saponin such as QuilA, a purified saponin such as QS21, QS7 or QS17, β-escin or digitonin;

immunostimulatory oligonucleotides comprising unmethylated CpG dinucleotides such as [purine-purine-CG-pyrimidine-pyrimidine] oligonucleotides. Immunostimulatory oligonucleotides may also be combined with cationic peptides as described, e.g., by Riedl et al. (2002);

Immune Stimulating Complexes together with saponins, for example Quil A (ISCOMS);

excipients and diluents, which are inherently non-toxic and non-therapeutic, such as water, saline, glycerol, ethanol, wetting or emulsifying agents, pH buffering substances, preservatives, and the like;

a biodegradable and/or biocompatible oil such as squalane, squalene, eicosane, tetratetracontane, glycerol, peanut oil, vegetable oil, in a concentration of, e.g., 1 to 10% or 2.5 to 5%;

vitamins such as vitamin C (ascorbic acid or its salts or esters), vitamin E (tocopherol), or vitamin A;

carotenoids, or natural or synthetic flavanoids;

trace elements, such as selenium;

any Toll-like receptor ligand as reviewed in Barton and Medzhitov (2002).

Any of the afore-mentioned adjuvants comprising 3-de-O-acetylated monophosphoryl lipid A, said 3-de-O-acetylated monophosphoryl lipid A may be forming a small particle (see International Patent Application Publication No. WO94/21292).

A "pharmaceutically acceptable vehicle" includes vehicles such as water, saline, physiological salt solutions, glycerol, ethanol, etc. Auxiliary substances such as wetting or emulsifying agents, pH buffering substances, preservatives may be included in such vehicles.

Typically, a vaccine composition is prepared as an injectable, either as a liquid solution or suspension. Injection may be subcutaneous, intramuscular, intravenous, intraperitoneal, intrathecal, intradermal, intraepidermal. Other types of administration comprise implantation, suppositories, oral ingestion, enteric application, inhalation, aerosolization or nasal spray or drops. Solid forms, optionally suitable for dissolving in, or suspension in, liquid vehicles prior to injection may also be prepared. The preparation may also be emulsified or encapsulated in liposomes for enhancing adjuvant effect.

Furthermore, the present invention relates to an antibody raised upon immunization of a mammal with at least one polypeptide or peptide as defined herein. In a specific embodiment, said antibody is specifically reactive with any of the polypeptides or peptides of the present invention. In a further specific embodiment, said antibody is a monoclonal antibody or a humanized antibody. Fragments of any of an antibody are also included in the term "antibody". Alternatively, antibodies to a polypeptide or part thereof according to the invention can be raised upon immunization of a mammal with a DNA vector comprising the open reading frame encoding said polypeptide or part thereof. The immunization process normally requires administration of a polypeptide or part thereof or derivative of any thereof to said mammal and/or administration of a DNA vector comprising the open reading frame encoding said polypeptide or part thereof to said mammal.

The monoclonal antibodies of the invention can be produced by any hybridoma liable to be formed according to classical methods from splenic cells of an animal, particularly from a mouse or rat, immunized against the HCV polypeptides according to the invention as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labeled by an appropriate label of the enzymatic, fluorescent, or radioactive type.

Non-human mammalian antibodies or animal antibodies can be humanized (see for instance Winter and Harris 1993). The antibodies or monoclonal antibodies according to the invention may be humanized versions of for instance rodent antibodies or rodent monoclonal antibodies made by means of recombinant DNA technology, departing from parts of rodent and/or human genomic DNA sequences coding for H and L chains or from cDNA clones coding for H and L chains.

Alternatively, the monoclonal antibodies according to the invention may be human monoclonal antibodies. These antibodies according to the present embodiment of the invention can also be derived from human peripheral blood lymphocytes of patients infected with the new HCV type according to the invention, or vaccinated against HCV. Such human monoclonal antibodies are prepared, for instance, by means of human peripheral blood lymphocytes (PBL) repopulation of severe combined immune deficiency (SCID) mice (for recent review, see Duchosal et al. 1992) or by screening Epstein Barr-virus-transformed lymphocytes of infected or vaccinated individuals for the presence of reactive B-cells by means of the antigens of the present invention.

The invention also relates to the use of the proteins or parts thereof or derivatives of any thereof for the selection of recombinant antibodies by the process of repertoire cloning (Persson et al., 1991).

The invention further relates to the use of an antibody according to the invention for the manufacture of an immunogenic composition or a vaccine composition. In particular the immunogenic composition is an HCV immunogenic composition and the vaccine composition is an HCV vaccine composition, a therapeutic HCV vaccine composition or a prophylactic HCV vaccine composition. Any of these compositions can be used for immunizing a mammal against HCV infection or for treating a mammal infected with HCV.

The invention also includes methods for detecting the presence of HCV antigens in a biological sample comprising the steps of:
  (i) contacting said biological sample with an antibody according to the invention under conditions allowing the formation of an immunological complex between HCV antigens and said antibody;
  (ii) detecting the immunological complex formed in (i);
  (iii) inferring from the immunological complex detected in (ii) the presence of HCV antigens present in said biological sample.

Another method of the invention is a method for typing of an HCV virus present in a biological sample comprising the steps of:
  (i) contacting said biological sample with an antibody according to the invention;
  (ii) detecting the immunological complex formed in (i) between the HCV antigens present in said biological sample and said antibody;
  (iii) inferring from the immunological complex detected in (ii) the type of HCV virus present in said biological sample.

The invention also relates to a composition comprising at least one of an isolated nucleic acid or oligonucleotide according the invention, an isolated protein or peptide according to the invention, a recombinant vector according to the invention, or an antibody according to the invention; and at least one of a suitable carrier, adjuvant or vehicle.

The invention further relates to the use of an HCV nucleic acid or oligonucleotide according to the invention, an HCV protein or peptide according to the invention, a recombinant vector according to the invention and/or an antibody according to the invention for the manufacture of an immunogenic composition or a vaccine composition. In particular the immunogenic composition is an HCV immunogenic composition and the vaccine composition is an HCV vaccine composition, a therapeutic HCV vaccine composition or a prophylactic HCV vaccine composition. Any of these compositions can be used for immunizing a mammal against HCV infection or for treating a mammal infected with HCV.

Further aspects of the current invention comprise any of the HCV immunogenic compositions, HCV vaccine compositions, prophylactic HCV vaccine compositions and/or therapeutic HCV vaccine compositions according to the invention for; or alternatively comprises the use of any of said compositions for:
  inducing in a mammal a humoral response to the HCV peptides comprised in any of said compositions; and/or
  inducing in a mammal a cellular response to the HCV peptides comprised in any of said compositions, wherein said cellular response may be a $CD4^+$ T-cell proliferation response and/or a $CD8^+$ cytotoxic T-cell response and/or the increased production of cytokines; and/or
  prophylactic protection of a mammal against chronic HCV infection, wherein said HCV infection may be a homologous or a heterologous HCV infection; and/or
  therapeutically treating a chronically HCV-infected mammal, wherein said HCV may be a homologous or a heterologous HCV; and/or
  reducing liver disease in an HCV-infected mammal; and/or
  reducing liver disease in a chronic HCV-infected mammal by at least 2 points according to the overall Ishak score; and/or
  reducing serum liver enzyme activity levels in an HCV-infected mammal, wherein said liver enzyme may be, e.g., alanine aminotransferase (ALT) or gamma-glutamylpeptidase; and/or
  reducing HCV RNA levels in an HCV-infected mammal; and/or
  reducing liver fibrosis progression in an HCV-infected mammal; and/or
  reducing liver fibrosis in an HCV-infected mammal; and/or
  reducing HCV antigen levels in or presented on liver cells, wherein said HCV antigens include E2 or Core antigens.

Said mammal obviously may be a human. In particular, the uses according to the invention are methods for obtaining at least one of the recited effects, with said methods comprising administering any of said compositions to a mammal or a human. The recited effects may be obtained in combination with a DNA vaccine or with a DNA vector or DNA vaccine vector capable of expressing or effectuating expression of one or more antigens. A DNA vaccine, DNA vector or DNA vaccine vector may be an HCV DNA vaccine, HCV DNA vector or HCV DNA vaccine vector (see further).

With "prophylactic protection against infection by a homologous HCV" is meant that protection is obtained against a challenge HCV virus of exactly the same genotype, subtype or isolate as compared to the HCV genotype, subtype or isolate from which the HCV antigen or HCV antigens are derived. A composition may for example comprise a peptide or polypeptide according to the present invention that is derived from a particular HCV type 1b isolate. A "homologous HCV" would in this case be the same particular HCV type 1b isolate. "Homologous" in the context of "therapeutic treatment of an HCV homologous to the HCV peptides in a composition" has to be interpreted likewise.

With "prophylactic protection against infection by a heterologous HCV" is meant that protection is obtained against a challenge HCV virus classified in another genotype, subtype, or isolate as compared to the HCV genotype, subtype or isolate from which the HCV antigen or HCV antigens are derived. A composition may for example comprise a peptide or polypeptide according to the present invention that is derived from a particular HCV type 1b isolate. A "heterologous HCV" would in this case be, e.g., an HCV type 1b isolate sufficiently different from the type 1b isolate from which the antigens were derived, a type I a HCV virus or a type 7 HCV virus. "Sufficiently different" as used in this particular context is to be understood at least a difference of 2%, 3% or 4% on the amino acid level. "Heterologous" in the context of "therapeutic treatment of an HCV heterologous to the HCV peptides in a composition" has to be interpreted likewise.

With the term "liver disease" is meant in this context any abnormal liver condition caused by infection with the hepatitis C virus including steatosis, inflammation, portal inflammation, fibrosis, perisinusoidal fibrosis, cirrhosis, necrosis, necro-inflammation, hepatocellular carcinoma, lobular hepatitis, interface hepatitis, periportal hepatitis, confluent necrosis and focal or portal inflammation.

With "reducing liver disease" is meant any stabilization or reduction of the liver disease status. Liver disease can be determined, e.g., by the Knodell scoring system (Knodell et al. 1981) or the Knodell scoring system adapted by Ishak (Ishak et al. 1995). A reduction of this score by two points is accepted as therapeutically beneficial effect in several studies (see, e.g., studies published after 1996 as indicated in Table 2 of Shiffman 1999).

With "reducing liver fibrosis progression" is meant any slowing down, halting or reverting of the normally expected progression of liver fibrosis. Liver fibrosis progression can be determined, e.g., by the Metavir scoring system. Normal expected progression of liver fibrosis according to this system was published to be an increase of the Metavir score of an untreated chronic HCV patient of approximately 0.133 per year (Poynard et al. 1997). "Reducing liver fibrosis" is meant to comprise any reduction of the normally expected progression of liver fibrosis.

Liver fibrosis and inflammation can be scored according to the Ishak scoring system (which is a modification of the scoring system of Knodell et al. 1981; Ishak et al. 1995) or Metavir scoring system (Bedossa and Poynard 1996). The Ishak scores range from 0 to 18 for grading of inflammation and from 0 to 6 for staging of fibrosis/cirrhosis. The sum of the Ishak inflammation and fibrosis scores comes closest to the Histological Activity Index (HAI; Knodell et al. 1981) which has been widely used. The Metavir scores range from 0 to 3 for grading of inflammation and from 0 to 4 for staging of fibrosis/cirrhosis. The overall progression rate of the Metavir score in an untreated patient is estimated to be 0.133 per year (Poynard et al. 1997).

Another aspect of the invention relates to an isolated HCV virus that is characterized by a genome comprising an HCV nucleic acid sequence of a nucleic acid or oligonucleotide according to the invention.

The invention further relates to a method for determining the genotype of an HCV nucleic acid or oligonucleotide according to the invention comprising the identification of the regions −100 to −92 and −128 to −118 in the 5' non-coding region of the genome of said virus. Said method can further comprise identification of at least one of the regions −138 to −132 or −240 to −233 in the 5' non-coding region of the genome of said virus. In particular, said region −100 to −92 is defined by SEQ ID NO:11 or the complement thereof or any thereof wherein "T" is replaced by "U". In particular, said region −128 to −118 is defined by SEQ ID NO:12 or the complement thereof or any thereof wherein "T" is replaced by "U". In particular, said region −138 to −132 is defined by SEQ ID NOs:13 or 14 or the complement thereof or any thereof wherein "T" is replaced by "U". In particular, said region −240 to −223 is defined by SEQ ID NO: 15 or the complement thereof or any thereof wherein "T" is replaced by "U". The regions specified above are to be understood to include all nucleotides of that region. For instance, the region −100 to −92 in the 5' non-coding region of the genome of an HCV virus is to be understood to include all nucleotides from relative position −100 to, and including, relative position −92.

With "identification of a region" is meant the identification of the nucleic acid sequence of said region by any possible nucleic acid detection method as described above, thus including for instance hybridization and sequencing.

EXAMPLES

Example 1

Genotyping of the Samples with the VERSANT® HCV Genotyping Assay (LiPA)

RNA isolation, cDNA Synthesis, PCR, and genotyping using the VERSANT® HCV Genotyping Assay (LiPA) were performed on two serum samples (IG93305 and IG93306) originating from chronic HCV patients with African ethnicity as described by the manufacturer (Innogenetics NV, Zwijnaarde, Belgium, distributed by Bayer Diagnostics). On the LiPA strips, unusual line patterns, which could not be attributed to any described genotype, were seen.

Example 2

Sequencing of the NS5B Region of Samples IG93305 and IG93306

For the determination of the sequence of the NS5B region of IG93305 and IG93306, a 400 bp NS5B fragment was amplified using primers HCPr292 and HCPr295, followed by a nested PCR with primers HCPr293 and HCPr294, resulting in a final NS5B fragment of 380 bp. This NS5B PCR fragment was isolated from a 1.5% LMT (low melting temperature) agarose gel and used for cycle sequencing using primers HCPr293 and HCPr294. The resulting NS5B nucleic acid sequence (SEQ ID NO 1 for IG93305 and SEQ ID NO 2 for IG93306) is depicted in FIG. 1. The amino acid sequence deduced thereof (sequence (SEQ ID NO 3 for IG93305 and SEQ ID NO 4 for IG93306) is also shown in FIG. 1. For 5' extension of the NS5B sequence a number of sense primers in the NS5A region upstream of SEQ ID NO:2 were designed. PCR with the combination of one of these sense primers (primer 1005032; SEQ ID NO:18) and a reverse primer designed on SEQ ID NO:2 (primer 1004177; SEQ ID NO:19) on reverse-transcribed (60 min at 55° C.) HCV RNA yielded a product of the expected size as judged by gel electrophoresis. The presumed correct product was excised from the agarose gel and sequenced. One of the determined nucleotide sequences comprised SEQ ID NO:2 in its 3' end and is designated herein SEQ ID NO:16 (FIG. 2). The amino acid sequence deduced thereof is designated herein SEQ ID NO:17 (FIG. 2). The primers used for cloning are depicted below in Table 1.

TABLE 1

Primers used for amplification and sequencing of the NS5B region.

| SEQ ID NO: | Primer | Primer sequence (5' to 3') |
|---|---|---|
| 5 | HCPr292 | CCGTATGGGGTTCTCGTATGA |
| 6 | HCPr293 | TATGACACCCGCTGCTTTGACTC |
| 7 | HCPr294 | CCTGGTCATAGCCTCCGTGAA |
| 8 | HCPr295 | GGGGCCGAGTACCTGGTCAT |
| 18 | 1005032 | CCATGCCCCCCCTYGAGGGRGARCC |
| 19 | 1004177 | CTTGCTCTCGCAAATGAGCACCAGGTCATC |

Example 3

Phylogenetic Analysis

Phylogenetic analysis was performed using the PHYLIP software package (Felsenstein 1993). Previously published sequences were taken from the EMBL/Genbank database (genotype 1: Genbank Accession Nos: M62321 (1a), D10749 (1a), D90208 (1b) and D14197 (1c); genotype 2: D00944 (2a), D50409 (2c), L29634 (2d), D49780 (2e), L44601 (2f), L48499 (2l) and D86532 (2j); genotype 3: D17763 (3a);

genotype 4: Y11604 (4a) and L29614 (4c); genotype 5: Y13184 (5a) and AF064490 (5a); genotype 6: L38379 (6a) and D84262 (6b); genotype 7: L38381 (7a) and D84263 (7b); genotype 8: D87357 (8a) and D84264 (8b); genotype 9: D87352 (9a) and AB027609 (9b); genotype 10: D26387 (10a); and genotype 11: D63822 (11a)) and used as reference sequences covering all known clades/genotypes and their most important subtypes. Alignments were created using the CLUSTAL X program (version 1.8; Thompson et al. 1994). Distance matrices were produced by DNADIST using the Kimura two-parameter setting and further analysed in NEIGHBOR, using the neighbor joining setting. The significance of clustering was evaluated by bootstrapping (1,000 replicates), using the programs SEQBOOT and CONSENSE. Bootstrap values ≧75% were considered significant. The resulting phylogenetic tree is depicted in FIG. 2.

Example 4

Identification of IG93305 and IG93306 as Belonging to a New HCV Genotype within a New HCV Clade Isolates IG93305 and IG93306 did not cluster with any of the known 11 genotypes of the 6 clades currently known for HCV (see FIG. 2 in Example 3). A clear separate branch was formed independent from any known HCV virus clades/genotypes, encompassing both isolates IG93305 and IG93306. A phylogenetic distance matrix with prototype sequences of all known HCV clades/genotypes (Table 2) was prepared by DNADIST using the Kimura two-parameter setting (PHYLIP software package version 3.5; Felsenstein 1993). Using a 340 bp NS5B fragment, phylogenetic distance boundaries were established for different types (phylogenetic distance>0,328), same type but different subtypes (phylogenetic distance between 0,127 and 0,328) and same subtype (<0,127) (Maertens and Stuyver 1997). According to these criteria, both isolates IG93305 and IG93306 belong to a new HCV genotype within a new clade (minimum distance is 0,439 with the genotype 2a prototype isolate (Accession number D00944). Furthermore, both isolates represent different subtypes (subtypes a and b) within the new genotype (phylogenetic distance with each other 0,185).

TABLE 2

Phylogenetic distance matrix of the NS5B nucleic acid regions of isolates IG93305 and IG93306 versus indicated reference sequences of all known clades/genotypes and their major subtypes.

| Genotype (Clade) | Subtype | GenBank Accession No | Virus isolate | Availability complete genome sequence | NS5B region IG93306 | NS5B region IG93305 |
|---|---|---|---|---|---|---|
| | | | IG93306 | | 0.000 | 0.185 |
| | | | IG93305 | | 0.185 | 0.000 |
| 1(1) | a | M62321 | HCV-1 | x | 0.542 | 0.472 |
| | a | D10749 | HC-J1 | x | 0.563 | 0.479 |
| | b | D90208 | HCV-J | x | 0.677 | 0.659 |
| | c | D14197 | HC-G9 | x (D14853) | 0.618 | 0.538 |
| 2(2) | a | D00944 | HC-J6 | x | 0.507 | 0.439 |
| | c | D50409 | BEBE1 | x | 0.503 | 0.531 |
| | d | L29634 | NE92 | — | 0.530 | 0.537 |
| | e | D49780 | JK151 | — | 0.582 | 0.529 |
| | f | L44601 | nl33 | — | 0.580 | 0.556 |
| | l | L48499 | HN4 | — | 0.542 | 0.513 |
| | j | D86532 | RU169 | — | 0.548 | 0.485 |
| 3(3) | a | D17763 | NZL1 | x | 0.563 | 0.523 |
| 4(4) | a | Y11604 | ED43 | x | 0.532 | 0.477 |
| | c | L29614 | GB48 | — | 0.490 | 0.492 |
| 5(5) | a | Y13184 | EUH1480 | x | 0.616 | 0.561 |
| | a | AF064490 | SA13 | x | 0.603 | 0.561 |
| 6(6) | a | L38379 | VN11 | — | 0.543 | 0.487 |
| | b | D84262 | Th580 | x | 0.605 | 0.572 |
| 7(6) | a | L38381 | VN13 | — | 0.492 | 0.504 |
| | b | D84263 | VN235 | x | 0.578 | 0.574 |
| 8(6) | a | D87357 | VN507 | — | 0.467 | 0.499 |
| | b | D84264 | VN405 | x | 0.553 | 0.548 |
| 9(6) | a | D87352 | VN004 | — | 0.578 | 0.517 |
| | b | AB027609 | Th555 | x | 0.543 | 0.550 |
| 10(3) | a | D26387 | Td3/93 | — | 0.626 | 0.630 |
| 11(6) | a | D63822 | JK046 | x | 0.530 | 0.503 | x: available;
—: not available

Example 5

Sequencing of the 5'NCR Region of Samples IG93305 and IG93306

For the determination of the sequence of the 5'NCR regions of IG93305 and IG93306, a 300 bp 5'NCR fragment was amplified as described in Stuyver et al. (1996). This PCR fragment was subsequently cloned in a pGEM-T vector (Promega Corp., USA) and clones were sequenced using vector SP6/T7 primers. The resulting 5' NCR sequences are depicted in FIG. 3 (SEQ ID NO: 9 for IG93305 and SEQ ID NO:10 for IG93306). Nucleotide differences between the two sequences are double underlined. The regions suited for genotyping of the HCV isolates IG93305 and IG93306 wherein said genotyping is based on the 5'NCR were identified and are indicated in Table 3.

TABLE 3

5'NCR regions suited for genotyping of HCV isolates fitting in the new HCV clade/genotype identified in the current invention.

| Region in 5'NCR | Sequence | SEQ ID NO: |
|---|---|---|
| −100 to −92 | CGAGACTGC | 11 |
| −128 to −118 | TATGCCCGGAG | 12 |
| −138 to −132 | TAACCCA | 13 |
| −138 to −132 | AAACCCA | 14 |
| −240 to −233 | GTCGTAGA | 15 |

REFERENCES

1. Altschul, S. F., Gish, W., Miller, W., Myers, E. W. & Lipman, D. J. Basic local alignment search tool. *J. Mol. Biol.* 215, 403-410 (1990).
2. Altschul, S. F. Amino acid substitution matrices from an information theoretic perspective. *J. Mol. Biol.* 219, 555-565 (1991).
3. Barton, G. M. & Medzhitov, R. Toll-like receptors and their ligands. *Curr. Top. Microbiol. Immunol.* 270, 81-92 (2002).
4. Beaucage, S. L. & Caruthers, M. H. Deoxynucleoside phosphoramidites—A new class of key intermediates for deoxypolynucleotide synthesis. *Tetrahedron Lett* 22, 1859-1862 (1981).
5. Bedossa, P. & Poynard, T. An algorithm for the grading of activity in chronic hepatitis C. The METAVIR Cooperative Study Group. *Hepatology* 24, 289-293 (1996).
6. Beekman, N. J. et al. Synthetic peptide vaccines: palmitoylation of peptide antigens by a thioester bond increases immunogenicity. *J. Pept. Res.* 50, 357-364 (1997).
7. Bej, A. K. et al. Multiplex PCR amplification and immobilized capture probes for detection of bacterial pathogens and indicators in water. *Mol Cell Probes* 4, 353-365 (1990).
8. Burns, J., Butler, J. & Whitesides, G. Selective reduction of disulfides by Tris(2-carboxyethyl)phosphine. *J. Org. Chem.* 56, 2648-2650 (1991).
9. Cairns, M. J., King, A. & Sun, L. Q. Nucleic acid mutation analysis using catalytic DNA. *Nucleic Acids Res* 28, E9 (2000).
10. Candotti, D., Temple, J., Sarkodie, F. & Allain, J. P. Frequent recovery and broad genotype 2 diversity characterize hepatitis C virus infection in Ghana, West Africa. *J. Virol.* 77, 7914-7923 (2003).
11. Church, G. M. & Gilbert, W. Genomic sequencing. *Proc Natl Acad Sci USA* 81, 1991-1995 (1984).
12. Cusi, M. G., Valassina, M. & Valensin, P. E. Comparison of M-MLV reverse transcriptase and Tth polymerase activity in RT-PCR of samples with low virus burden. *Biotechniques* 17, 1034-1036 (1994).
13. Darbre, A. Practical protein chemistry: a handbook. Whiley & Sons Ltd., (1986).
14. Drmanac, R. et al. DNA sequence determination by hybridization: a strategy for efficient large-scale sequencing. *Science* 260, 1649-1652 (1993).
15. Duchosal, M. A. et al. Immunization of hu-PBL-SCID mice and the rescue of human monoclonal Fab fragments through combinatorial libraries. *Nature* 355, 258-262 (1992).
16. Felsenstein, J. PHYLIP (Phylogeny Inference Package) version 3.5c. Distributed by the author. Department of Genetics, University of Washington, Seattle, Wash., USA. (1993).
17. Gailit, J. Restoring free sulfhydryl groups in synthetic peptides. *Anal. Biochem.* 214, 334-335 (1993).
18. Grakoui, A., Wychowski, C., Lin, C., Feinstone, S. M. & Rice, C. M. Expression and identification of hepatitis C virus polyprotein cleavage products. *J. Virol.* 67, 1385-1395 (1993).
19. Griffin, T. J. & Smith, L. M. Single-nucleotide polymorphism analysis by MALDI-TOF mass spectrometry. *Trends. Biotechnol.* 18, 77-84 (2000).
20. Hacia, J. G., Brody, L. C., Chee, M. S., Fodor, S. P. & Collins, F. S. Detection of heterozygous mutations in BRCA1 using high density oligonucleotide arrays and two-colour fluorescence analysis. *Nat Genet* 14, 441-447 (1996).
21. Healey, B. G., Matson, R. S. & Walt, D. R. Fiberoptic DNA sensor array capable of detecting point mutations. *Anal. Biochem* 251, 270-279 (1997).
22. Hermanson, G. T. Bioconjugate techniques. Academic Press, San Diego (1996).
23. Holmgren, A. Thioredoxin catalyzes the reduction of insulin disulfides by dithiothreitol and dihydrolipoamide. *J. Biol. Chem.* 254, 9627-9632 (1979).
24. Ishak, K. et al. Histological grading and staging of chronic hepatitis. *J. Hepatol.* 22, 696-699 (1995).
25. Jacobs, K. A. et al. The thermal stability of oligonucleotide duplexes is sequence independent in tetraalkylammonium salt solutions: application to identifying recombinant DNA clones. *Nucleic Acids Res* 16, 4637-4650 (1988).
26. James, W. & al-Shamkhani, A. RNA enzymes as tools for gene ablation. *Curr Opin. Biotechnol.* 6, 44-49 (1995).
27. Johnson, D. A. et al. Synthesis and biological evaluation of a new class of vaccine adjuvants: aminoalkyl glucosaminide 4-phosphates (AGPs). *Bioorg. Med. Chem Lett* 9, 2273-2278 (1999).
28. Kenney, M., Ray, S. & Boles, T. C. Mutation typing using electrophoresis and gel-immobilized Acrydite probes. *Biotechniques* 25, 516-521 (1998).
29. Kimura, M. A simple method for estimating evolutionary rates of base substitutions through comparative studies of nucleotide sequences. *J. Mol Evol.* 16, 111-120 (1980).
30. Knodell, R. G. et al. Formulation and application of a numerical scoring system for assessing histological activity in asymptomatic chronic active hepatitis. *Hepatology* 1, 431-435 (1981).

31. Kumar, N., Kella, D. & Kinsella, J. E. A method for the controlled cleavage of disulfide bonds in proteins in the absence of denaturants. *J. Biochem. Biophys. Methods* 11, 251-263 (1985).
32. Kumar, N., Kella, D. & Kinsella, J. E. Anomalous effects of denaturants on sulfitolysis of protein disulfide bonds. Int. *J. Peptide Prot. Res.* 28, 586-592 (1986).
33. Kwok, S. et al. Effects of primer-template mismatches on the polymerase chain reaction: human immunodeficiency virus type 1 model studies. *Nucleic Acids Res* 18, 999-1005 (1990).
34. Maertens, G. & Stuyver, L. The molecular medicine of viral hepatitis. Harrison, T. J. & Zuckerman, A. J. (eds.), pp. 183-233 (John Wiley & Sons, 1997).
35. Majzoub, J. A., Rich, A., van Boom, J. & Habener, J. F. Vasopressin and oxytocin mRNA regulation in the rat assessed by hybridization with synthetic oligonucleotides. *J. Biol. Chem.* 258, 14061-14064 (1983).
36. Meller, A., Nivon, L., Brandin, E., Golovchenko, J. & Branton, D. Rapid nanopore discrimination between single polynucleotide molecules. *Proc Natl Acad Sci USA* 97, 1079-1084 (2000).
37. Myers, T. W. & Gelfand, D. H. Reverse transcription and DNA amplification by a *Thermus thermophilus* DNA polymerase. *Biochemistry* 30, 7661-7666 (1991).
38. Persing, D. et al. Taking toll: lipid A mimetics as adjuvants and immunomodulators. *Trends Microbiol.* 10, S32 (2002).
39. Persson, M. A., Caothien, R. H. & Burton, D. R. Generation of diverse high-affinity human monoclonal antibodies by repertoire cloning. *Proc. Natl. Acad. Sci. U.S.A* 88, 2432-2436 (1991).
40. Pomroy, N. C. & Deber, C. M. Solubilization of hydrophobic peptides by reversible cysteine PEGylation. Biochem. *Biophys. Res. Commun.* 245, 618-621 (1998).
41. Poynard, T., Bedossa, P. & Opolon, P. Natural history of liver fibrosis progression in patients with chronic hepatitis C. The OBSVIRC, METAVIR, CLINIVIR, and DOSVIRC groups. *Lancet* 349, 825-832 (1997).
42. Rein, A. et al. Inactivation of murine leukemia virus by compounds that react with the zinc finger in the viral nucleocapsid protein. *J. Virol.* 70, 4966-4972 (1996).
43. Riedl, P., Buschle, M., Reimann, J. & Schirmbeck, R. Binding immune-stimulating oligonucleotides to cationic peptides from viral core antigen enhances their potency as adjuvants. *Eur. J. Immunol.* 32, 1709-1716 (2002).
44. Robertson, B. et al. Classification, nomenclature, and database development for hepatitis C virus (HCV) and related viruses: proposals for standardization. International Committee on Virus Taxonomy. *Arch Virol.* 143, 2493-2503 (1998).
45. Saiki, R. K. et al. Primer-directed enzymatic amplification of DNA with a thermostable DNA polymerase. *Science* 239, 487-491 (1988).
46. Saiki, R. K., Walsh, P. S., Levenson, C. H. & Erlich, H. A. Genetic analysis of amplified DNA with immobilized sequence-specific oligonucleotide probes. *Proc Natl Acad Sci USA* 86, 6230-6234 (1989).
47. Saitou, N. & Nei, M. The neighbor-joining method: a new method for reconstructing phylogenetic trees. *Mol. Biol. Evol.* 4, 406-425 (1987).
48. Salemi, M. & Vandamme, A. M. Hepatitis C virus evolutionary patterns studied through analysis of full-genome sequences. *J. Mol Evol.* 54, 62-70 (2002).
49. Sambrook, J., Fritsch, E. F. & Maniatis, T. Molecular Cloning: A Laboratory Manual. Cold Spring Harbor Laboratory Press, (1989).
50. Sapolsky, R. J. et al. High-throughput polymorphism screening and genotyping with high-density oligonucleotide arrays. *Genet Anal.* 14, 187-192 (1999).
51. Shiffman, M. L. Improvement in liver histopathology associated with interferon therapy in patients with chronic hepatitis C. *Viral Hepatitis Reviews* 5, 27-43 (1999).
52. Shimotohno, K. et al. Processing of the hepatitis C virus precursor protein. *J. Hepatol.* 22, 87-92 (1995).
53. Singh, R. & Kats, L. Catalysis of reduction of disulfide by selenol. *Anal. Biochem.* 232, 86-91 (1995).
54. Smith, R. D., Cheng, X., Bruce, J. E., Hofstadler, S. A. & Anderson, G. A. Trapping detection and reaction of very large single molecular ions by mass spectrometry. *Nature* 369, 137-139 (1994).
55. Sreevatsan, S. et al. Algorithmic approach to high-throughput molecular screening for alpha interferon-resistant genotypes in hepatitis C patients. *J Clin Microbiol* 36, 1895-1901 (1998).
56. States, D. J., Gish, W. & Altschul, S. F. Improved sensitivity of nucleic acid database searches using application-specific scoring matrices. *Methods* 3, 66-70 (1991).
57. Stuyver, L., Wyseur, A., Van Arnhem, W., Hernandez, F. & Maertens, G. Second-generation line probe assay for hepatitis C virus genotyping. *J. Clin. Microbiol.* 34, 2259-2266 (1996).
58. Stuyver, L. et al. Line probe assay for rapid detection of drug-selected mutations in the human immunodeficiency virus type 1 reverse transcriptase gene. *Antimicrob Agents Chemother* 41, 284-291 (1997).
59. Tateno, Y., Takezaki, N. & Nei, M. Relative efficiencies of the maximum-likelihood, neighbor-joining, and maximum-parsimony methods when substitution rate varies with site. *Mol. Biol. Evol.* 11, 261-277 (1994).
60. Thakur, M. L., DeFulvio, J., Richard, M. D. & Park, C. H. Technetium-99m labeled monoclonal antibodies: evaluation of reducing agents. *Int. J. Rad. Appl. Instrum. B* 18, 227-233 (1991).
61. Thompson, J. D., Higgins, D. G. & Gibson, T. J. CLUSTAL W: improving the sensitivity of progressive multiple sequence alignments through sequence weighting, position-specific gap penalties and weight matrix choice. *Nucleic Acids Res* 22, 4673-4680 (1994).
62. Vingerhoeds, M. H. et al. Immunoliposomes as enzyme-carriers (immuno-enzymosomes) for antibody-directed enzyme prodrug therapy (ADEPT): optimization of prodrug activating capacity. *Pharm. Res.* 13, 604-610 (1996).
63. Walewski, J. L., Keller, T. R., Stump, D. D. & Branch, A. D. Evidence for a new hepatitis C virus antigen encoded in an overlapping reading frame. *RNA.* 7, 710-721 (2001).
64. Whitcombe, D., Theaker, J., Guy, S. P., Brown, T. & Little, S. Detection of PCR products using self-probing amplicons and fluorescence. *Nat Biotechnol.* 17, 804-807 (1999).
65. Winter, G. & Harris, W. J. Humanized antibodies. *Immunol. Today* 14, 243-246 (1993).
66. Xu, Z. et al. Synthesis of a novel hepatitis C virus protein by ribosomal frameshift. *EMBO J.* 20, 3840-3848 (2001).

All documents cited herein are incorporated in their entirety herein by reference.

The invention claimed is:

1. An isolated nucleic acid comprising an HCV nucleic acid sequence of an HCV, said HCV being characterized in that its phylogenetic distance from at least one of the following nucleic acid sequences is less than or equal to 0.328:
   the nucleic acid of SEQ ID NOs: 1, 2, or 16,
   the nucleic acid sequence encoding the protein of SEQ ID NOs: 3, 4 or 17,
   the full length complement of the nucleic acid sequence of SEQ ID NOs: 1, 2, or 16, or
   the full length complement of the nucleic acid sequence encoding the protein of SEQ ID NOs: 3, 4 or 17;
   wherein said HCV nucleic acid sequence comprises at least one nucleotide that is different from the corresponding nucleotide in an HCV nucleic acid sequence of an HCV of any of clades 1 to 6;
   wherein said nucleic acid is DNA, cDNA or a synthetic nucleic acid, or wherein said nucleic acid is RNA and wherein "T" is replaced by "U".

2. An isolated nucleic acid comprising an HCV nucleic acid sequence, said HCV nucleic acid sequence being selected from the following nucleic acid sequences:
   the nucleic acid sequence set forth in SEQ ID NO:1, 2, 9, 10, or 16,
   the nucleic acid sequence encoding the protein set forth in SEQ ID NO: 3, 4 or 17,
   the full length complement of the nucleic acid sequence set forth in SEQ ID NO:1, 2, 9, 10, or 16, or
   the full length complement of the nucleic acid sequence encoding the protein set forth in SEQ ID NO: 3, 4 or 17;
   wherein the nucleic acid sequence set forth in SEQ ID NO:1 or 9, or the full length complement of a nucleic acid sequence set forth in SEQ ID NO:1 or 9, are a different HCV subtype the nucleic acid sequence set forth in SEQ ID NO:2, 10 or 16, or the full length complement of a nucleic acid sequence set forth in SEQ ID NO:2, 10, or 16;

wherein said nucleic acid is DNA, cDNA or a synthetic nucleic acid, or wherein said nucleic acid is RNA and wherein "T" is replaced by "U".

3. The isolated nucleic acid according to claim 1 or 2 which is a primer.

4. The isolated nucleic acid according to claim 1 or 2 which is a probe.

5. The isolated nucleic acid according to claim 1 or 2, further comprising
one or more modified nucleotide bases;
one or more labeled nucleotides;
one or more peptide nucleic acid monomers;
one or more locked nucleic acid monomers; or
a modified nucleic acid backbone.

6. A recombinant vector comprising a nucleic acid according to claim 1 or 2.

7. The recombinant vector according to claim 6 which is an expression vector capable of directing expression of an HCV protein encoded by the nucleic acid.

8. A host cell transformed with a nucleic acid according to claim 1 or 2 or with a recombinant vector comprising said nucleic acid.

9. A diagnostic kit for detecting the presence and/or for determining the genotype of an HCV virus in a biological sample, said kit comprising at least one of a nucleic acid according to claim 1 or 2.

10. The diagnostic kit according to claim 9 wherein said nucleic is attached to a solid support.

11. A composition comprising at least one of a nucleic acid according to claim 1 or 2; and at least one of a suitable carrier, adjuvant or vehicle.

12. A composition comprising a vector of claim 6 and at least one carrier.

13. A composition of claim 12, said composition being immunogenic.

14. A method for the recombinant production of a protein or peptide comprising the steps of:
(i) transformation of an appropriate cellular host with a recombinant vector comprising a nucleic acid according to claim 1 or 2 and encoding said protein or peptide;
(ii) culturing the transformed cellular host of (i) under conditions enabling the expression of said protein;
(iii) harvesting the protein expressed in (ii).

15. A panel of probes comprising a probe of claim 4.

16. A method for detecting the presence of an HCV virus in a biological sample comprising the step of detecting the presence of a nucleic acid according to claim 1 or 2.

17. A method for determining the genotype of an HCV virus in a biological sample comprising the step of detecting the presence of a nucleic acid according to claim 1 or 2.

18. The method according to claim 16 wherein the detection of the presence of the nucleic acid comprises at least one of an amplification reaction, a sequencing reaction, a hybridization reaction or a reverse hybridization reaction.

19. The method according to claim 17 wherein the detection of the presence of the nucleic acid comprises at least one of an amplification reaction, a sequencing reaction, a hybridization reaction or a reverse hybridization reaction.

20. The method according to claim 16 wherein the detection of the presence of the nucleic acid comprises:
amplification of the nucleic acid with an oligonucleotide;
hybridization or reverse hybridization of the nucleic acid with an oligonucleotide; or
detection of the nucleic acid with an oligonucleotide.

21. The method according to claim 17 wherein the detection of the presence of the nucleic acid comprises:
amplification of the nucleic acid with an oligonucleotide;
hybridization or reverse hybridization of the nucleic acid with an oligonucleotide; or
detection of the nucleic acid with an oligonucleotide.

22. A method for detecting the presence of an HCV virus in a biological sample comprising the steps of:
(i) obtaining a target HCV nucleic acid from a biological sample suspected to contain a nucleic acid sequence according to claim 1 or 2;
(ii) obtaining the nucleic acid of the target HCV nucleic acid of (i);
(iii) inferring from the nucleic acid sequence obtained in (ii) the presence of a nucleic acid according to claim 1 or 2 and, therefrom, the presence of an HCV virus in said biological sample.

23. A method for detecting the presence of an HCV virus in a biological sample comprising the steps of:
(i) obtaining a target HCV nucleic acid from a biological sample suspected to contain a nucleic acid according to claim 1 or 2;
(ii) contacting the target HCV nucleic acid of (i) with an oligonucleotide, and said contacting generating a discriminatory signal;
(iii) inferring from the discriminatory signal obtained in (ii) the presence of the nucleic acid of claim 1 or 2 and, therefrom, the presence of an HCV virus in said biological sample.

24. A method for determining the genotype of an HCV virus in a biological sample comprising the steps of:
(i) obtaining a target HCV nucleic acid from a biological sample suspected to contain a nucleic acid according to claim 1 or 2;
(ii) obtaining the nucleic acid sequence of the target HCV nucleic acid of (i);
(iii) inferring from the nucleic acid sequence obtained in (ii) the presence of the nucleic acid of claim 1 or 2, and, therefrom, the genotype of said HCV virus in said biological sample.

25. A method for detecting the genotype of an HCV virus in a biological sample comprising the steps of:
(i) obtaining a target HCV nucleic acid from a biological sample suspected to contain a nucleic acid according to claim 1 or 2;
(ii) contacting the target HCV nucleic acid of (i) with an oligonucleotide, and said contacting generating a discriminatory signal;
(iii) inferring from the discriminatory signal obtained in (ii) the presence of the nucleic acid of claim 1 or 2, and, therefrom, the genotype of said HCV virus in said biological sample.

* * * * *

SEQUENCE LISTING

<160> NUMBER OF SEQ ID NOS: 19

<210> SEQ ID NO 1
<211> LENGTH: 345
<212> TYPE: DNA
<213> ORGANISM: hepatitis C virus

<400> SEQUENCE: 1

```
cagtcacaga acaagacatt cgcactgaga ctgacatcta tcagtgctgt aaccttgacc      60
ctgaggctcg caccgtaatc acctccctca ctgagagatt gtacgtgggt ggccccatgt     120
tcaactctag gggcgagaag gttggctaca ggaggtgcag agccagtggt gtattcccca     180
ctagcatggg gaacaccatg acgtgctata tcaaggcctt ggcagccagc aaggctgcag     240
gcttggtagg cgcggatttc ctggtgtgtg cgatgacttg gttgtcatc tgcgagagca      300
ggggagtcga gcaggacaaa gcggatctgc aagcctttcac ggatg                    345
```

<210> SEQ ID NO 2
<211> LENGTH: 343
<212> TYPE: DNA
<213> ORGANISM: hepatitis C virus

<400> SEQUENCE: 2

```
cagttacaga acaagacatt cgcactgaga ctgccatcta tcagtgctgc aacctcgacc      60
ccgaggctcg caccgctatt gacgccctca ccgagagatt gtacgtgggt ggtcccatgt     120
tcaactccaa aggtgagaag gtcggataca gaaggtgcag agccagtgga gttttcccca     180
ccagcatggg gaacaccatg acgtgctaca taaaagccaa gcggccagc gcggccgcgg       240
gcttgagtgg cgccgatttc ctagtctgtg cgatgaccct ggtggtcatt tgcgagagca     300
agggtgtcga tcaggatagg gcggctctga gctttcac gga                         343
```

<210> SEQ ID NO 3
<211> LENGTH: 114
<212> TYPE: PRT
<213> ORGANISM: hepatitis C virus

<400> SEQUENCE: 3

Val Thr Glu Gln Asp Ile Arg Thr Glu Thr Asp Ile Tyr Gln Cys Cys
 1               5                  10                  15

Asn Leu Asp Pro Glu Ala Arg Thr Val Ile Thr Ser Leu Thr Glu Arg
            20                  25                  30

Leu Tyr Val Gly Gly Pro Met Phe Asn Ser Arg Gly Glu Lys Val Gly
        35                  40                  45

Tyr Arg Arg Cys Arg Ala Ser Gly Val Phe Pro Thr Ser Met Gly Asn
    50                  55                  60

Thr Met Thr Cys Tyr Ile Lys Ala Leu Ala Ala Ser Lys Ala Ala Gly
65                  70                  75                  80

Leu Val Gly Ala Asp Phe Leu Val Cys Gly Asp Asp Leu Val Val Ile
                85                  90                  95

Cys Glu Ser Arg Gly Val Glu Gln Asp Lys Ala Asp Leu Gln Ala Phe
            100                 105                 110

Thr Asp

<210> SEQ ID NO 4
<211> LENGTH: 113
<212> TYPE: PRT
<213> ORGANISM: hepatitis C virus -continued

<400> SEQUENCE: 4

Val Thr Glu Gln Asp Ile Arg Thr Glu Thr Ala Ile Tyr Gln Cys Cys
1               5                   10                  15

Asn Leu Asp Pro Glu Ala Arg Thr Ala Ile Asp Ala Leu Thr Glu Arg
            20                  25                  30

Leu Tyr Val Gly Gly Pro Met Phe Asn Ser Lys Gly Glu Lys Val Gly
        35                  40                  45

Tyr Arg Arg Cys Arg Ala Ser Gly Val Phe Pro Thr Ser Met Gly Asn
    50                  55                  60

Thr Met Thr Cys Tyr Ile Lys Ala Lys Ala Ala Ser Ala Ala Ala Gly
65                  70                  75                  80

Leu Ser Gly Ala Asp Phe Leu Val Cys Gly Asp Asp Leu Val Val Ile
            85                  90                  95

Cys Glu Ser Lys Gly Val Asp Gln Asp Arg Ala Ala Leu Arg Ala Phe
            100                 105                 110

Thr

<210> SEQ ID NO 5
<211> LENGTH: 21
<212> TYPE: DNA
<213> ORGANISM: artificial sequence
<220> FEATURE:
<223> OTHER INFORMATION: HCPr292

<400> SEQUENCE: 5
ccctatgggc ttctcgtatg a                                          21

<210> SEQ ID NO 6
<211> LENGTH: 23
<212> TYPE: DNA
<213> ORGANISM: artificial sequence
<220> FEATURE:
<223> OTHER INFORMATION: HCPr293

<400> SEQUENCE: 6
tatgacaccc gctgctttga ctc                                        23

<210> SEQ ID NO 7
<211> LENGTH: 21
<212> TYPE: DNA
<213> ORGANISM: artificial sequence
<220> FEATURE:
<223> OTHER INFORMATION: HCPr294

<400> SEQUENCE: 7
cctggtcata gcctccgtga a                                          21

<210> SEQ ID NO 8
<211> LENGTH: 20
<212> TYPE: DNA
<213> ORGANISM: artificial sequence
<220> FEATURE:
<223> OTHER INFORMATION: HCPr295

<400> SEQUENCE: 8
ggggccgagt acctggtcat                                            20

<210> SEQ ID NO 9
<211> LENGTH: 239
<212> TYPE: DNA
<213> ORGANISM: hepatitis C virus -continued

<400> SEQUENCE: 9
tttctagcca tggcgttagt atgagtgtcg tacagcctcc aggaccccccc ctcccgggag    60 agccatagtg gtctgcggaa ccggtgagta caccggaatt gccgggaaga ctgggtcctt   120
tcttggatta acccactcta tgcccggaga tttgggcgtg cccccgcgag actgctagcc   180
gagtagtgtt gggtcgcgaa aggccttgtg gtactgcctg atagggtgct tgcgagtga    239

<210> SEQ ID NO 10
<211> LENGTH: 239
<212> TYPE: DNA
<213> ORGANISM: hepatitis C virus

<400> SEQUENCE: 10
tttctagcca tggcgttagt atgagtgtcg tacagcctcc aggaccccccc ctcccgggag    60 agccatagtg gtctgcggaa ccggtgagta caccggaatt gccgggaaga ctgggtcctt   120
tcttggataa acccactcta tgcccggaga tttgggcgtg cccccgcgag actgctagcc   180
gagtagtgtt gggtcgcgaa aggccttgtg gtactgcctg atagggtgct tgcgagtga    239

<210> SEQ ID NO 11
<211> LENGTH: 9
<212> TYPE: DNA
<213> ORGANISM: hepatitis C virus

<400> SEQUENCE: 11 cgagactgc                                                             9

<210> SEQ ID NO 12
<211> LENGTH: 11
<212> TYPE: DNA
<213> ORGANISM: hepatitis C virus

<400> SEQUENCE: 12
tatgcccgga g                                                         11

<210> SEQ ID NO 13
<211> LENGTH: 7
<212> TYPE: DNA
<213> ORGANISM: hepatitis C virus

<400> SEQUENCE: 13 taaccca                                                               7

<210> SEQ ID NO 14
<211> LENGTH: 7
<212> TYPE: DNA
<213> ORGANISM: hepatitis C virus

<400> SEQUENCE: 14 aaaccca                                                               7

<210> SEQ ID NO 15
<211> LENGTH: 8
<212> TYPE: DNA
<213> ORGANISM: hepatitis C virus

<400> SEQUENCE: 15 gtcgtaca                                                              8

<210> SEQ ID NO 16
<211> LENGTH: 1060
<212> TYPE: DNA

-continued

<213> ORGANISM: hepatitis C virus

<400> SEQUENCE: 16

```
ggtcaacagt cagcgaacgy tccgagcgtg tttgctgttc aatgtcctac tcatggacgg      60
gagccttagt gacgccctcc ggaccggagg aggaaaggct tccgataaat gccctgagca     120
acaccatgct acggcattac aacatggttt acagcacaac atcacgctcg ccgctcaga     180
gggcaaagaa agtgactttt gacagactgc aagttctcga tgaccactac aagagaacgc    240
tcgatgacgt caaggctaag gccgctggcg ttaccgcacg tttgctcacc ttggaggagg    300
ctgccgctct tactccgacc cactccgcga gatctaagtt cgggtatggg gcgaaggatg    360
tgagagctct cgcccccaag gcagtgactg acataaaagg agtctggaag aacttgctta    420
ctgacaagac taccccgata ccgacttcaa taatggccaa gaatgaggtc ttctgtgtta    480
accctgcyaa gggagggaaa aaaccagcta gactgattgt atacctgac ttaggcgtcc     540
gggtgtgcga gaagcgagcg ctgtacgatc tagcgcaaaa gcttcctcag gccgttatgg    600
ggtccgcata cggttccaa tactcacctg ctcagcgggt tgatctcctg gttaagacgt     660
gggagtccaa acgcactccc atgggctttt catatgatac ccgctgtttt gactctacag    720
ttacagaaca agacattcgc actgagactg ccatctatca gtgctgcaac ctcgaccccg    780
aggctcgcac cgctattgac gccctcaccg agagattgta cgtgggtggt cccatgttca    840
actccaaagg tgagaaggtc ggatacagaa ggtgcagagc cagtggagtt ttccccacca    900
gcatggggaa caccatgacg tgctacataa aagccaaggc ggccagcgcg ccgcgggct     960
tgagtggcgc cgatttccta gtctgtggcg atgacctggt ggtcatttgc gagagcaagg   1020
gtgtcgatca ggatagggcg gctctgagag cttttcacgga                        1060
```

<210> SEQ ID NO 17
<211> LENGTH: 352
<212> TYPE: PRT
<213> ORGANISM: hepatitis C virus

<400> SEQUENCE: 17

```
Ser Thr Val Ser Glu Arg Ser Glu Arg Val Cys Cys Ser Met Ser Tyr
1               5                   10                  15

Ser Trp Thr Gly Ala Leu Val Thr Pro Ser Gly Pro Glu Glu Glu Arg
            20                  25                  30

Leu Pro Ile Asn Ala Leu Ser Asn Thr Met Leu Arg His Tyr Asn Met
        35                  40                  45

Val Tyr Ser Thr Thr Ser Arg Ser Ala Ala Gln Arg Ala Lys Lys Val
    50                  55                  60

Thr Phe Asp Arg Leu Gln Val Leu Asp Asp His Tyr Lys Arg Thr Leu
65                  70                  75                  80

Asp Asp Val Lys Ala Lys Ala Ala Gly Val Thr Ala Arg Leu Leu Thr
                85                  90                  95

Leu Glu Glu Ala Ala Ala Leu Thr Pro Thr His Ser Ala Arg Ser Lys
            100                 105                 110

Phe Gly Tyr Gly Ala Lys Asp Val Arg Ala Leu Ala Pro Lys Ala Val
        115                 120                 125

Thr Asp Ile Lys Gly Val Trp Lys Asn Leu Leu Thr Asp Lys Thr Thr
    130                 135                 140

Pro Ile Pro Thr Ser Ile Met Ala Lys Asn Glu Val Phe Cys Val Asn
145                 150                 155                 160

Pro Ala Lys Gly Gly Lys Lys Pro Ala Arg Leu Ile Val Tyr Pro Asp
                165                 170                 175
```

```
Leu Gly Val Arg Val Cys Glu Lys Arg Ala Leu Tyr Asp Leu Ala Gln
            180                 185                 190

Lys Leu Pro Gln Ala Val Met Gly Ser Ala Tyr Gly Phe Gln Tyr Ser
        195                 200                 205

Pro Ala Gln Arg Val Asp Leu Val Lys Thr Trp Glu Ser Lys Arg
    210                 215                 220

Thr Pro Met Gly Phe Ser Tyr Asp Thr Arg Cys Phe Asp Ser Thr Val
225                 230                 235                 240

Thr Glu Gln Asp Ile Arg Thr Glu Thr Ala Ile Tyr Gln Cys Cys Asn
                245                 250                 255

Leu Asp Pro Glu Ala Arg Thr Ala Ile Asp Ala Leu Thr Glu Arg Leu
            260                 265                 270

Tyr Val Gly Gly Pro Met Phe Asn Ser Lys Gly Glu Lys Val Gly Tyr
            275                 280                 285

Arg Arg Cys Arg Ala Ser Gly Val Phe Pro Thr Ser Met Gly Asn Thr
    290                 295                 300

Met Thr Cys Tyr Ile Lys Ala Lys Ala Ala Ser Ala Ala Ala Gly Leu
305                 310                 315                 320

Ser Gly Ala Asp Phe Leu Val Cys Gly Asp Asp Leu Val Val Ile Cys
                325                 330                 335

Glu Ser Lys Gly Val Asp Gln Asp Arg Ala Ala Leu Arg Ala Phe Thr
            340                 345                 350

<210> SEQ ID NO 18
<211> LENGTH: 25
<212> TYPE: DNA
<213> ORGANISM: artificial sequence
<220> FEATURE:
<223> OTHER INFORMATION: primer1005032

<400> SEQUENCE: 18
ccatgccccc cctygagggr garcc                                      25

<210> SEQ ID NO 19
<211> LENGTH: 30
<212> TYPE: DNA
<213> ORGANISM: artificial sequence
<220> FEATURE:
<223> OTHER INFORMATION: primer1004177

<400> SEQUENCE: 19
cttgctctcg caaatgacca ccaggtcatc                                 30
```